United States Patent
Aboytes

(10) Patent No.: US 9,931,495 B2
(45) Date of Patent: Apr. 3, 2018

(54) DEVICES AND METHODS FOR VASCULAR RECANALIZATION

(71) Applicant: Covidien LP, Mansfield, MA (US)

(72) Inventor: Maria Aboytes, Palo Alto, CA (US)

(73) Assignee: COVIDIEN LP, Mansfield, MA (US)

(*) Notice: Subject to any disclaimer, the term of this patent is extended or adjusted under 35 U.S.C. 154(b) by 0 days.

(21) Appl. No.: 14/666,054

(22) Filed: Mar. 23, 2015

(65) Prior Publication Data
US 2015/0196744 A1  Jul. 16, 2015

Related U.S. Application Data

(63) Continuation of application No. 13/033,100, filed on Feb. 23, 2011, now Pat. No. 9,211,396.
(Continued)

(51) Int. Cl.
*A61M 29/00* (2006.01)
*A61M 29/02* (2006.01)
(Continued)

(52) U.S. Cl.
CPC .............. *A61M 29/02* (2013.01); *A61B 17/22* (2013.01); *A61B 17/221* (2013.01); *A61F 2/013* (2013.01);
(Continued)

(58) Field of Classification Search
CPC ........... A61B 2017/00778; A61B 2017/00867; A61B 2017/22054; A61B 2017/22055;
(Continued)

(56) References Cited

U.S. PATENT DOCUMENTS 2,548,602 A   4/1951  Greenburg
3,435,826 A   4/1969  Fogarty
(Continued)

FOREIGN PATENT DOCUMENTS

JP   H06-190049 A   7/1994
JP   2004-097807 A   4/2004
(Continued)

OTHER PUBLICATIONS

Fannelop, T. et al., "Multidose Cold Oxygenated Blood Is Superior to a Single Dose of Bretschneider HTK-Cardioplegia in the Pig", The Annals of Thoracic Surgery, vol. 87, No. 4, Apr. 2009, pp. 1205-1213.
(Continued)

*Primary Examiner* — Diane Yabut
*Assistant Examiner* — Martin T. Ton
(74) *Attorney, Agent, or Firm* — Fortem IP LLP; Mary Fox

(57) ABSTRACT

In some embodiments, a medical device for recanalizing a vessel having a blockage and restoring blood flow through an obstructed blood vessel includes an expandable member coupled to a core wire and a hypotube that are movable relative to each other to manipulate the expandable member between various configurations. The expandable member having a capture structure in an expanded configuration. The expandable member can include multiple interstices formed by woven mesh filaments or braided strands through which the material blocking the vessel can pass. The capture structure can include a shape on its external surface that facilitates dislodgement and capture of the material within capture spaces created by the expandable member. Some embodiments include a capture sack or cap for capturing material and preventing material from migrating down stream of the blockage. Superoxygenated blood can be
(Continued)

infused distal to the blockage to minimize loss of function during an ischemic event.

17 Claims, 19 Drawing Sheets

Related U.S. Application Data

(60) Provisional application No. 61/306,951, filed on Feb. 23, 2010.

(51) Int. Cl.
    *A61F 2/01*     (2006.01)
    *A61B 17/22*     (2006.01)
    *A61B 17/221*     (2006.01)
    *A61M 25/00*     (2006.01)
    *A61M 25/06*     (2006.01)
    *A61B 17/00*     (2006.01)
    *A61M 25/10*     (2013.01)

(52) U.S. Cl.
    CPC .............. *A61B 2017/00778* (2013.01); *A61B 2017/00867* (2013.01); *A61B 2017/2212* (2013.01); *A61B 2017/2215* (2013.01); *A61B 2017/22038* (2013.01); *A61B 2017/22054* (2013.01); *A61B 2017/22055* (2013.01); *A61F 2002/018* (2013.01); *A61F 2230/0006* (2013.01); *A61F 2230/008* (2013.01); *A61F 2230/0067* (2013.01); *A61F 2230/0069* (2013.01); *A61F 2230/0076* (2013.01); *A61M 25/0074* (2013.01); *A61M 25/10* (2013.01); *A61M 2025/0004* (2013.01); *A61M 2025/0681* (2013.01); *A61M 2025/109* (2013.01)

(58) Field of Classification Search
    CPC .. A61B 2017/22038; A61B 2017/2212; A61B 2017/2215; A61B 17/22; A61M 2025/109
    USPC ......................... 606/191, 194, 200; 604/104
    See application file for complete search history.

(56) References Cited

U.S. PATENT DOCUMENTS

| | | | |
|---|---|---|---|
| 3,438,375 A | 4/1969 | Ericson | |
| 3,613,664 A | 10/1971 | Willson et al. | |
| 3,773,034 A | 11/1973 | Burns et al. | |
| 3,923,065 A | 12/1975 | Nozick et al. | |
| 4,030,503 A | 6/1977 | Clark, III | |
| 4,248,234 A | 2/1981 | Assenza et al. | |
| 4,650,466 A | 3/1987 | Luther | |
| 4,762,130 A | 8/1988 | Fogarty et al. | |
| 4,873,978 A | 10/1989 | Ginsburg | |
| 4,883,458 A | 11/1989 | Shiber | |
| 4,890,611 A | 1/1990 | Monfort et al. | |
| 4,909,787 A | 3/1990 | Danforth | |
| 4,921,484 A | 5/1990 | Hillstead | |
| 4,936,312 A | 6/1990 | Tsukagoshi | |
| 4,976,690 A | 12/1990 | Solar et al. | |
| 4,998,539 A | 3/1991 | Delsanti | |
| 5,002,560 A | 3/1991 | Machold et al. | |
| 5,009,659 A | 4/1991 | Hamlin et al. | |
| 5,011,488 A | 4/1991 | Ginsburg | |
| 5,034,001 A | 7/1991 | Garrison et al. | |
| 5,059,178 A | 10/1991 | Ya | |
| 5,102,415 A | 4/1992 | Guenther et al. | |
| 5,129,910 A | 7/1992 | Phan et al. | |
| 5,192,286 A | 3/1993 | Phan et al. | |
| 5,192,290 A | 3/1993 | Hilal | |
| 5,226,888 A | 7/1993 | Arney | |
| 5,320,604 A | 6/1994 | Walker et al. | |
| 5,370,653 A | 12/1994 | Cragg | |
| 5,423,771 A | 6/1995 | Imran | |
| 5,437,632 A | 8/1995 | Engelson | |
| 5,470,322 A | 11/1995 | Horzewski et al. | |
| 5,476,450 A | 12/1995 | Ruggio | |
| 5,484,424 A | 1/1996 | Cottenceau et al. | |
| 5,490,859 A | 2/1996 | Mische et al. | |
| 5,501,694 A | 3/1996 | Ressemann et al. | |
| 5,573,520 A | 11/1996 | Schwartz et al. | |
| 5,619,993 A | 4/1997 | Lee | |
| 5,653,722 A | 8/1997 | Kieturakis | |
| 5,681,335 A | 10/1997 | Serra et al. | |
| 5,695,507 A | 12/1997 | Auth et al. | |
| 5,746,758 A | 5/1998 | Nordgren et al. | |
| 5,749,849 A | 5/1998 | Engelson | |
| 5,749,858 A | 5/1998 | Cramer | |
| 5,795,322 A | 8/1998 | Boudewijn | |
| 5,827,304 A | 10/1998 | Hart | |
| 5,868,708 A | 2/1999 | Hart et al. | |
| 5,882,329 A | 3/1999 | Patterson et al. | |
| 5,895,400 A | 4/1999 | Abela | |
| 5,902,263 A | 5/1999 | Patterson et al. | |
| 5,904,698 A | 5/1999 | Thomas et al. | |
| 5,928,186 A | 7/1999 | Homsma et al. | |
| 5,972,019 A | 10/1999 | Engelson et al. | |
| 6,001,118 A | 12/1999 | Daniel et al. | |
| 6,027,520 A | 2/2000 | Tsugita et al. | |
| 6,030,397 A | 2/2000 | Monetti et al. | |
| 6,066,149 A * | 5/2000 | Samson et al. | ............... 606/159 |
| 6,066,158 A | 5/2000 | Engelson et al. | |
| 6,090,118 A | 7/2000 | McGuckin, Jr. | |
| 6,106,488 A | 8/2000 | Fleming et al. | |
| 6,146,339 A | 11/2000 | Biagtan et al. | |
| 6,146,396 A | 11/2000 | Konya et al. | |
| 6,168,579 B1 | 1/2001 | Ross | |
| 6,221,006 B1 | 4/2001 | Dubrul et al. | |
| 6,238,412 B1 | 5/2001 | Dubrul et al. | |
| 6,254,571 B1 * | 7/2001 | Hart | ...................... A61B 17/221 |
| | | | 604/107 |
| 6,258,115 B1 | 7/2001 | Dubrul | |
| 6,322,534 B1 | 11/2001 | Shkolnik | |
| 6,383,205 B1 | 5/2002 | Samson et al. | |
| 6,398,708 B1 | 6/2002 | Hastings et al. | |
| 6,454,775 B1 | 9/2002 | Demarais et al. | |
| 6,458,139 B1 | 10/2002 | Palmer et al. | |
| 6,494,884 B2 | 12/2002 | Gifford, III et al. | |
| 6,514,273 B1 | 2/2003 | Voss et al. | |
| 6,544,279 B1 | 4/2003 | Hopkins et al. | |
| 6,562,021 B1 | 5/2003 | Derbin et al. | |
| 6,575,995 B1 | 6/2003 | Huter et al. | |
| 6,582,417 B1 | 6/2003 | Ledesma et al. | |
| 6,602,264 B1 | 8/2003 | McGuckin, Jr. | |
| 6,605,102 B1 | 8/2003 | Mazzocchi et al. | |
| 6,626,861 B1 * | 9/2003 | Hart | ................. A61B 17/22032 |
| | | | 604/96.01 |
| 6,635,070 B2 | 10/2003 | Leeflang et al. | |
| 6,638,245 B2 | 10/2003 | Miller et al. | |
| 6,645,222 B1 | 11/2003 | Parodi et al. | |
| 6,652,548 B2 | 11/2003 | Evans et al. | |
| 6,660,013 B2 | 12/2003 | Rabiner et al. | |
| 6,663,650 B2 | 12/2003 | Sepetka et al. | |
| 6,679,860 B2 | 1/2004 | Stiger | |
| 6,685,722 B1 | 2/2004 | Rosenbluth et al. | |
| 6,692,504 B2 | 2/2004 | Kurz et al. | |
| 6,695,858 B1 | 2/2004 | Dubrul et al. | |
| 6,699,260 B2 | 3/2004 | Dubrul et al. | |
| 6,702,782 B2 | 3/2004 | Miller et al. | |
| 6,702,840 B2 | 3/2004 | Keller et al. | |
| 6,746,468 B1 | 6/2004 | Sepetka et al. | |
| 6,746,475 B1 | 6/2004 | Rivelli, Jr. | |
| 6,758,851 B2 | 7/2004 | Shiber | |
| 6,767,353 B1 | 7/2004 | Shiber | |
| 6,814,739 B2 | 11/2004 | Secrest et al. | |
| 6,818,002 B2 | 11/2004 | Shiber | |
| 6,824,545 B2 | 11/2004 | Sepetka et al. | |
| 6,840,949 B2 | 1/2005 | Barbut | |
| 6,843,798 B2 | 1/2005 | Kusleika et al. | |
| 6,855,137 B2 | 2/2005 | Bon | |
| 6,860,899 B1 | 3/2005 | Rivelli, Jr. | |
| 6,887,235 B2 | 5/2005 | O'Connor et al. | |

(56) References Cited

U.S. PATENT DOCUMENTS

| | | |
|---|---|---|
| 6,890,341 B2 | 5/2005 | Dieck et al. |
| 6,905,503 B2 | 6/2005 | Gifford, III et al. |
| 6,926,725 B2 | 8/2005 | Cooke et al. |
| 6,945,977 B2 | 9/2005 | Demarais et al. |
| 7,004,954 B1 | 2/2006 | Voss et al. |
| 7,008,434 B2 | 3/2006 | Kurz et al. |
| 7,037,316 B2 | 5/2006 | McGuckin, Jr. et al. |
| 7,052,500 B2 | 5/2006 | Bashiri et al. |
| 7,066,931 B2 | 6/2006 | O'Connor et al. |
| 7,101,362 B2 | 9/2006 | Vanney |
| 7,179,273 B1 | 2/2007 | Palmer et al. |
| 7,220,269 B1 | 5/2007 | Ansel et al. |
| 7,244,243 B2 | 7/2007 | Lary |
| 7,285,126 B2 | 10/2007 | Sepetka et al. |
| 7,320,698 B2 | 1/2008 | Eskuri |
| 7,323,001 B2 | 1/2008 | Clubb et al. |
| 7,374,561 B2 | 5/2008 | Barbut |
| 7,534,252 B2 | 5/2009 | Sepetka et al. |
| 7,578,830 B2 | 8/2009 | Kusleika et al. |
| 7,766,049 B2 | 8/2010 | Miller et al. |
| 7,766,921 B2 | 8/2010 | Sepetka et al. |
| 7,887,560 B2 | 2/2011 | Kuselika |
| 7,938,820 B2 | 5/2011 | Webster et al. |
| 7,993,302 B2 | 8/2011 | Hebert et al. |
| 7,993,363 B2 | 8/2011 | Demond et al. |
| 8,043,313 B2 | 10/2011 | Krolik et al. |
| 8,052,640 B2 | 11/2011 | Fiorella et al. |
| 8,057,496 B2 | 11/2011 | Fischer, Jr. |
| 8,066,757 B2 | 11/2011 | Ferrera et al. |
| 8,070,791 B2 | 12/2011 | Ferrera et al. |
| 8,075,510 B2 | 12/2011 | Aklog et al. |
| 8,092,486 B2 | 1/2012 | Berrada et al. |
| 8,100,935 B2 | 1/2012 | Rosenbluth et al. |
| 8,118,829 B2 | 2/2012 | Carrison et al. |
| 8,246,641 B2 | 8/2012 | Osborne et al. |
| 8,303,612 B2 | 11/2012 | Nakao et al. |
| 8,480,697 B2 | 7/2013 | Kucharczyk et al. |
| 8,715,314 B1 | 5/2014 | Janardhan et al. |
| 8,753,371 B1 | 6/2014 | Janardhan et al. |
| 8,771,289 B2* | 7/2014 | Mohiuddin .......... A61B 17/221 606/127 |
| 8,784,434 B2 | 7/2014 | Rosenbluth et al. |
| 8,801,749 B2 | 8/2014 | Adams et al. |
| 8,814,892 B2 | 8/2014 | Galdonik et al. |
| 8,845,678 B1 | 9/2014 | Janardhan et al. |
| 8,870,901 B1 | 10/2014 | Janardhan et al. |
| 8,968,330 B2 | 3/2015 | Rosenbluth et al. |
| 2001/0016726 A1 | 8/2001 | Dubrul et al. |
| 2001/0038807 A1 | 11/2001 | Barbut et al. |
| 2001/0051810 A1 | 12/2001 | Dubrul et al. |
| 2002/0032460 A1 | 3/2002 | Kusleika et al. |
| 2002/0058963 A1 | 5/2002 | Vale et al. |
| 2002/0111648 A1* | 8/2002 | Kusleika .......... A61F 2/01 606/200 |
| 2002/0115942 A1 | 8/2002 | Stanford et al. |
| 2002/0143349 A1 | 10/2002 | Gifford, III et al. |
| 2002/0143360 A1 | 10/2002 | Douk et al. |
| 2002/0147458 A1 | 10/2002 | Hiblar et al. |
| 2002/0169474 A1 | 11/2002 | Kusleika et al. |
| 2002/0177870 A1 | 11/2002 | Sepetka et al. |
| 2003/0023230 A1 | 1/2003 | Lewis et al. |
| 2003/0032977 A1 | 2/2003 | Brady |
| 2003/0040694 A1 | 2/2003 | Dorros et al. |
| 2003/0040704 A1 | 2/2003 | Dorros et al. |
| 2003/0040705 A1 | 2/2003 | Dorros et al. |
| 2003/0040762 A1 | 2/2003 | Dorros et al. |
| 2003/0042186 A1 | 3/2003 | Boyle |
| 2003/0055444 A1 | 3/2003 | Evans et al. |
| 2003/0060756 A1 | 3/2003 | Hayman et al. |
| 2003/0060782 A1 | 3/2003 | Bose et al. |
| 2003/0065354 A1 | 4/2003 | Boyle et al. |
| 2003/0176884 A1 | 9/2003 | Berrada et al. |
| 2003/0233117 A1 | 12/2003 | Adams et al. |
| 2004/0010280 A1 | 1/2004 | Adams et al. |
| 2004/0010282 A1 | 1/2004 | Kusleika |
| 2004/0073243 A1 | 4/2004 | Sepetka et al. |
| 2004/0098028 A1 | 5/2004 | Martinez |
| 2004/0115164 A1 | 6/2004 | Pierce et al. |
| 2004/0133232 A1 | 7/2004 | Rosenbluth et al. |
| 2004/0153117 A1 | 8/2004 | Clubb et al. |
| 2004/0161451 A1 | 8/2004 | Pierce et al. |
| 2004/0193246 A1 | 9/2004 | Ferrera |
| 2004/0199201 A1 | 10/2004 | Kellett et al. |
| 2004/0220663 A1 | 11/2004 | Rivelli, Jr. |
| 2005/0027287 A1 | 2/2005 | O'Connor et al. |
| 2005/0059995 A1 | 3/2005 | Sepetka et al. |
| 2005/0085849 A1 | 4/2005 | Sepetka et al. |
| 2005/0090845 A1 | 4/2005 | Boyd |
| 2005/0090857 A1 | 4/2005 | Kusleika et al. |
| 2005/0119686 A1 | 6/2005 | Clubb |
| 2005/0124973 A1 | 6/2005 | Dorros et al. |
| 2005/0149164 A1 | 7/2005 | Rivelli, Jr. |
| 2005/0182386 A1 | 8/2005 | Aggerholm |
| 2005/0222580 A1 | 10/2005 | Gifford, III et al. |
| 2005/0267323 A1 | 12/2005 | Dorros et al. |
| 2005/0267491 A1 | 12/2005 | Kellett et al. |
| 2005/0267568 A1 | 12/2005 | Berez et al. |
| 2005/0277979 A1 | 12/2005 | Dorros et al. |
| 2006/0004395 A1 | 1/2006 | Chiel et al. |
| 2006/0004405 A1 | 1/2006 | Salahieh et al. |
| 2006/0020286 A1 | 1/2006 | Niermann |
| 2006/0058836 A1 | 3/2006 | Bose et al. |
| 2006/0124530 A1 | 6/2006 | Gorsuch et al. |
| 2006/0195137 A1 | 8/2006 | Sepetka et al. |
| 2006/0258987 A1 | 11/2006 | Lentz et al. |
| 2006/0264907 A1 | 11/2006 | Eskridge et al. |
| 2006/0265036 A1 | 11/2006 | O'Connor et al. |
| 2006/0282111 A1 | 12/2006 | Morsi |
| 2007/0038226 A1 | 2/2007 | Galdonik et al. |
| 2007/0118165 A1 | 5/2007 | DeMello et al. |
| 2007/0161963 A1 | 7/2007 | Smalling |
| 2007/0179513 A1 | 8/2007 | Deutsch |
| 2007/0185500 A1 | 8/2007 | Martin et al. |
| 2007/0185501 A1 | 8/2007 | Martin et al. |
| 2007/0191866 A1 | 8/2007 | Palmer et al. |
| 2007/0197103 A1 | 8/2007 | Martin et al. |
| 2007/0198028 A1 | 8/2007 | Miloslavski et al. |
| 2007/0208361 A1 | 9/2007 | Okushi et al. |
| 2007/0208367 A1* | 9/2007 | Fiorella .......... A61B 17/22 606/198 |
| 2007/0213753 A1 | 9/2007 | Waller |
| 2007/0255252 A1 | 11/2007 | Mehta |
| 2007/0288054 A1 | 12/2007 | Tanaka et al. |
| 2008/0045881 A1 | 2/2008 | Teitelbaum et al. |
| 2008/0065012 A1 | 3/2008 | Hebert et al. |
| 2008/0082107 A1 | 4/2008 | Miller et al. |
| 2008/0109031 A1 | 5/2008 | Sepetka et al. |
| 2008/0167678 A1 | 7/2008 | Morsi |
| 2008/0177296 A1 | 7/2008 | Sepetka et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0183257 A1 | 7/2008 | Imran et al. |
| 2008/0188876 A1 | 8/2008 | Sepetka et al. |
| 2008/0188885 A1 | 8/2008 | Sepetka et al. |
| 2008/0215077 A1 | 9/2008 | Sepetka et al. |
| 2008/0234706 A1 | 9/2008 | Sepetka et al. |
| 2008/0234722 A1 | 9/2008 | Bonnette et al. |
| 2008/0262532 A1 | 10/2008 | Martin |
| 2008/0269774 A1 | 10/2008 | Garcia et al. |
| 2008/0269798 A1 | 10/2008 | Ramzipoor et al. |
| 2008/0300621 A1 | 12/2008 | Hopkins et al. |
| 2009/0024157 A1 | 1/2009 | Anukhin |
| 2009/0054918 A1 | 2/2009 | Henson |
| 2009/0062841 A1 | 3/2009 | Amplatz et al. |
| 2009/0076593 A1 | 3/2009 | Valaie |
| 2009/0082800 A1 | 3/2009 | Janardhan |
| 2009/0105722 A1 | 4/2009 | Fulkerson et al. |
| 2009/0105737 A1 | 4/2009 | Fulkerson et al. |
| 2009/0125053 A1 | 5/2009 | Ferrera et al. |
| 2009/0163846 A1 | 6/2009 | Aklog et al. |
| 2009/0163851 A1 | 6/2009 | Holloway et al. |
| 2009/0182361 A1 | 7/2009 | Thompson et al. |
| 2009/0182362 A1 | 7/2009 | Thompson et al. |

(56) References Cited

U.S. PATENT DOCUMENTS

| | | |
|---|---|---|
| 2009/0187209 A1 | 7/2009 | Cohen |
| 2009/0187211 A1 | 7/2009 | Mackiewicz |
| 2009/0240238 A1 | 9/2009 | Grodrian et al. |
| 2009/0248059 A1 | 10/2009 | Morsi |
| 2009/0287166 A1 | 11/2009 | Dang |
| 2009/0287292 A1 | 11/2009 | Becking et al. |
| 2009/0292297 A1 | 11/2009 | Ferrere |
| 2009/0292307 A1 | 11/2009 | Razack |
| 2009/0299393 A1 | 12/2009 | Martin et al. |
| 2009/0306755 A1* | 12/2009 | Dickinson ............... A61F 2/07 623/1.3 |
| 2010/0036410 A1 | 2/2010 | Krolik et al. |
| 2010/0082012 A1 | 4/2010 | Hattangadi et al. |
| 2010/0114113 A1 | 5/2010 | Dubrul et al. |
| 2010/0174269 A1 | 7/2010 | Tompkins et al. |
| 2010/0204634 A1 | 8/2010 | Baxter et al. |
| 2010/0204672 A1 | 8/2010 | Lockhart et al. |
| 2010/0217276 A1 | 8/2010 | Garrison et al. |
| 2010/0249815 A1 | 9/2010 | Jantzen et al. |
| 2010/0318178 A1 | 12/2010 | Rapaport et al. |
| 2011/0060212 A1 | 3/2011 | Slee et al. |
| 2011/0082490 A1 | 4/2011 | Connelly et al. |
| 2011/0152920 A1 | 6/2011 | Eckhouse et al. |
| 2011/0152993 A1 | 6/2011 | Marchand et al. |
| 2011/0160760 A1 | 6/2011 | Ferrera et al. |
| 2011/0172699 A1 | 7/2011 | Miller et al. |
| 2011/0190806 A1 | 8/2011 | Wittens |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0251629 A1 | 10/2011 | Galdonik et al. |
| 2012/0089216 A1 | 4/2012 | Rapaport et al. |
| 2012/0101510 A1 | 4/2012 | Lenker et al. |
| 2012/0143239 A1 | 6/2012 | Aklog et al. |
| 2012/0165919 A1 | 6/2012 | Cox et al. |
| 2012/0179181 A1 | 7/2012 | Straub et al. |
| 2012/0232655 A1 | 9/2012 | Lorrison et al. |
| 2012/0271231 A1 | 10/2012 | Agrawal |
| 2013/0018409 A1 | 1/2013 | Le et al. |
| 2013/0035628 A1 | 2/2013 | Garrison et al. |
| 2013/0131711 A1 | 5/2013 | Bowman |
| 2014/0005713 A1 | 1/2014 | Bowman |
| 2014/0155908 A1 | 1/2014 | Rosenbluth et al. |
| 2014/0046359 A1 | 2/2014 | Bowman et al. |
| 2014/0155980 A1 | 6/2014 | Turjman et al. |
| 2014/0188143 A1 | 7/2014 | Martin et al. |
| 2014/0260928 A1 | 9/2014 | Janardhan et al. |
| 2014/0343585 A1 | 11/2014 | Ferrera et al. |

FOREIGN PATENT DOCUMENTS

| | | |
|---|---|---|
| JP | 2005-230132 A | 9/2005 |
| JP | 2005-323702 A | 11/2005 |
| JP | 2006-094876 A | 4/2006 |
| JP | 2007-117760 A2 | 5/2007 |
| WO | 96/01591 A1 | 1/1996 |
| WO | 97/17889 A1 | 5/1997 |
| WO | 2005/046736 A2 | 5/2005 |
| WO | 2006/110186 A2 | 10/2006 |
| WO | 2006/127005 A1 | 11/2006 |
| WO | 2007/092820 A2 | 8/2007 |
| WO | 2008/063156 A2 | 5/2008 |
| WO | 2009/155571 A1 | 12/2009 |
| WO | 2010/010545 A1 | 1/2010 |
| WO | 2010/023671 A2 | 3/2010 |
| WO | 2010/049121 A2 | 5/2010 |
| WO | 2010/102307 A1 | 9/2010 |
| WO | 2011/054531 A2 | 5/2011 |
| WO | 2012/009675 A2 | 1/2012 |
| WO | 2012/065748 A1 | 5/2012 |
| WO | 2014/047650 A1 | 3/2014 |
| WO | 2014/081892 A1 | 5/2014 |

OTHER PUBLICATIONS

Gibbs, et al., "Temporary Stent as a bail-out device during percutaneous transluminal coronay angioplasty: preliminary clinical experience," British Heart Journal, 1994, 71:372-377, Oct. 12, 1993 (6 pgs.).

Goldhaber, S. et al. "Percutaneous Mechanical Thrombectomy for Acute Pulmonary Embolism—A Double-Edged Sword", American College of CHEST Physicians, Aug. 2007:132:2, 363-372, Northbrook, IL, USA.

Goldhaber, S., "Advanced treatment strategies for acute pulmonary embolism, including thrombolysis and embolectomy", Journal of Thrombosis and Haemostasis, 2009: 7 (Suppl. 1): 322-327, Cardiovascular Division, Department of Medicine, Brigham and Women's Hospital, Harvard Medical School, Boston, MA, USA.

Gupta, S. et al., "Acute Pulmonary Embolism Advances in Treatment", JAPI, Association of Physicians India, Mar. 2008, vol. 56, 185-191, Consultant Interventional Cardiologist, SDM Hospital, Jaipur, India; Consultant and Former Professor and Head of Dept. of Medicine, Armed Forces Medical College, Pune, India.

Konstantinides, S. et al., "Pulmonary embolism hotline 2012—Recent and expected trials", Thrombosis and Haemostasis, Jan. 9, 2013:33; 43-50, Center for Thrombosis and Haemostasis, Johannes Gutenberg University Medical Center, Mainz, Germany.

Konstantinides, S. et al., "Pulmonary embolism: risk assessment and management", European Society of Cardiology; European Heart Journal, Sep. 7, 2012:33, 3014-3022, Center for Thrombosis and Haemostasis, Johannes Gutenberg University Medical Center, Mainz, Germany.

Kucher, N. et al., "Management of Massive Pulmonary Embolism", Circulation, 2005:112:e28-e32; American Heart Association, Dallas, TX, USA.

Kucher, N. et al., "Percutaneous Catheter Thrombectomy Device for Acute Pulmonary Embolism: In Vitro and in Vivo Testing", Radiology, Sep. 2005:236:3 852-858; Cardiovascular Division of Brigham and Women's Hospital, Boston, MA, USA.

Kucher, N., "Catheter Interventions in Massive Pulmonary Embolism", CardiologyRounds, Mar. 2006 vol. 10, Issue 3; Cardiovascular Division of Brigham and Women's Hospital, Boston, MA, USA.

Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254, Northbrook, IL, USA.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009: 20:1431-1440, Stanford University Medical Center, Stanford, CA, USA.

Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179, Stanford University Medical Center, Stanford, CA, USA.

Lee, L. et al, "Massive pulmonary embolism: review of management strategies with a focus on catheter-based techniques", Expert Rev. Cardiovasc. Ther. 8(6), 863-873 (2010).

Liu, S. et al, "Massive Pulmonary Embolism: Treatment with the Rotarex Thrombectomy System", Cardiovascular Interventional Radiology; 2011: 34:106-113, Springer Science and Business Media, LLC and the Cardiovascular and Interventional Radiological Society of Europe.

Muller-Hulsbeck, S. et al. "Mechanical Thrombectomy of Major and Massive Pulmonary Embolism with Use of the Amplatz Thrombectomy Device", Investigative Radiology Jun. 2001:36:6:317-322, Department of Radiology, Christian Albrects University, Kiel, Germany.

(56) References Cited

OTHER PUBLICATIONS

Reekers, J. et al., "Mechanical Thrombectomy for Early Treatment of Massive Pulmonary Embolism", CardioVascular and Interventional Radiology, 2003:26:246-250, Springer-Verlag New York, Inc., NY, USA.

"ReStore™ Thrombectomy Microcatheter", Brochure from Reverse Medical Corporation, 2010, 2 pages.

Ribo, M. et al., "Buying Time for Recanalization in Acute Stroke: Arterial Blood Infusion Beyond the Occluding Clot as a Neuroprotective Strategy", Journal of Neuroimaging, Barcelona, Spain, Jan. 28, 2008, 4 pages.

Schmitz-Rode et al., "New Mesh Basket for Percutaneous Removal of Wall-Adherent Thrombi in Dialysis Shunts," Cardiovasc Intervent Radiol 16:7-10 (1993) 4 pgs.

Schmitz-Rode et al., "Temporary Pulmonary Stent Placement as Emergency Treatment of Pulmonary Embolism," Journal of the American College of Cardiology, 2006, vol. 48, No. 4, pp. 812-816.

Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380, Elsevier Science, Inc., New York NY, USA.

Tapson, V., "Acute Pulmonary Embolism", The New England Journal of Medicine, Mar. 6, 2008:358: 1037-52, Massachusetts Medical Society, MA, USA.

TherOx, Inc., "Data Shows Significant Infarct Size Reduction in Acute Myocardial Infarction Patients", Washington, DC, Oct. 23, 2007 (Press Release), 2 pages.

Truong et al., "Mechanical Thrombectomy of Iliocaval Thrombosis Using a Protective Expandable Sheath," Cardiovasc Intervent Radiol 27-254-258 (2004) 5 pgs.

Turk et al., "Adapt Fast study: a direct aspiration first pass technique for acute stroke thrombectomy." J NeuroIntervent Surg, 2014, vol. 6, pp. 260-264.

Uflacker, R., "Interventional Therapy for Pulmonary Embolism", Journal of Vascular and Interventional Radiology Feb. 2001: 12:147-164, Medical University of South Carolina, Charleston, SC, USA.

Verma, R., MD et al., "Evaluation of a Newly Developed Percutaneous Thrombectomy Basket Device in Sheep With Central Pulmonary Embolisms", Investigative Radiology, Oct. 2006; 41: 729-734, Lippincott Williams & Wilkins.

Wood, S., "AMIHOT II breathes new life into supersaturated oxygen strategy post-PCI", theheart.org by WebMD, Oct. 23, 2007, 2 pages.

International Search Report and Written Opinion dated Jul. 22, 2011, in International Application No. PCT/US2011/025926 (9 pages).

International Preliminary Report on Patentability dated Aug. 28, 2012, in International Application No. PCT/US2011/025926 (7 pages).

International Search Report for International App. No. PCT/US13/61470, dated Jan. 17, 2014, 2 pages.

International Search Report for International App. No. PCT/US13/71101, dated Mar. 31, 2014, 4 pages.

Non-final Office Action dated Jan. 2, 2013, in U.S. Appl. No. 13/033,100 (20 pages).

Non-Final Office Action in U.S. Appl. No. 13/843,742, dated Sep. 13, 2013, 16 pages.

Final Office Action dated Oct. 9, 2013, in U.S. Appl. No. 13/033,100 (20 pages).

Non-final Office Action dated Mar. 12, 2014, in U.S. Appl. No. 13/033,100 (24 pages).

Notice of Allowance for U.S. Appl. No. 13/843,742, dated Mar. 12, 2014, 13 pages.

Final Office Action dated Nov. 6, 2014, in U.S. Appl. No. 13/033,100 (15 pages).

\* cited by examiner

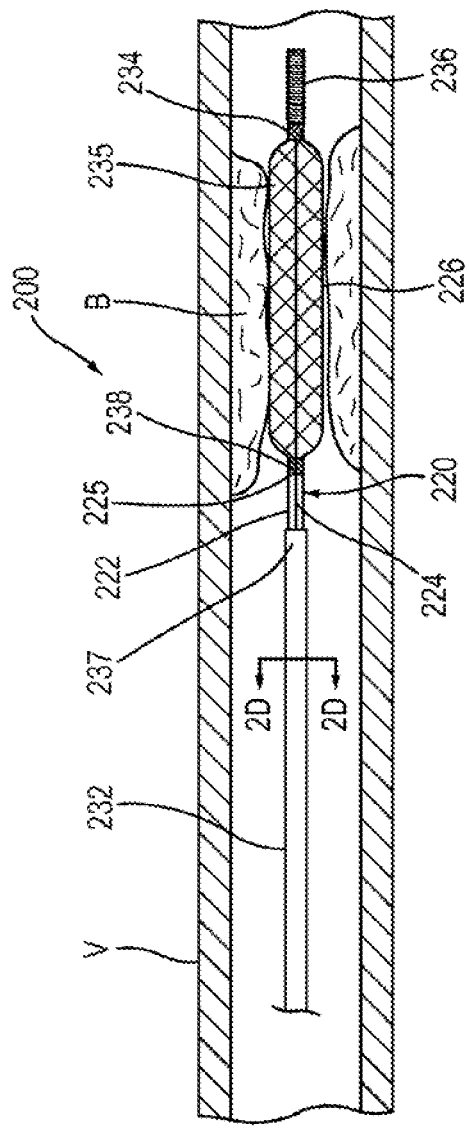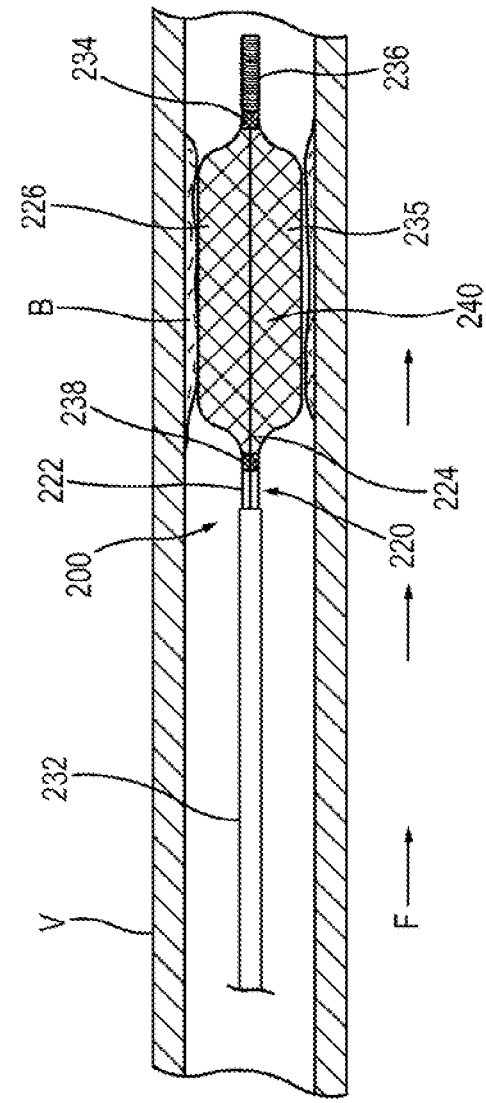
FIG. 2A
FIG. 2B

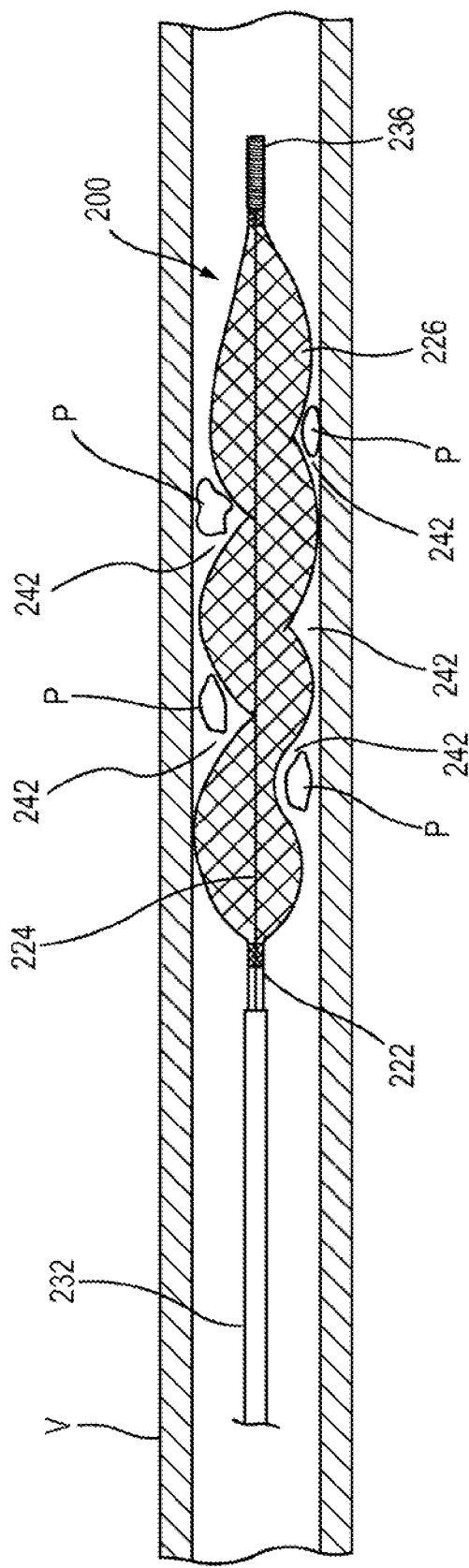
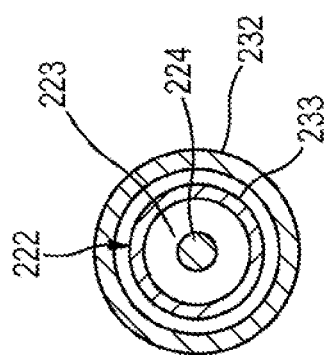
FIG. 2C
FIG. 2D

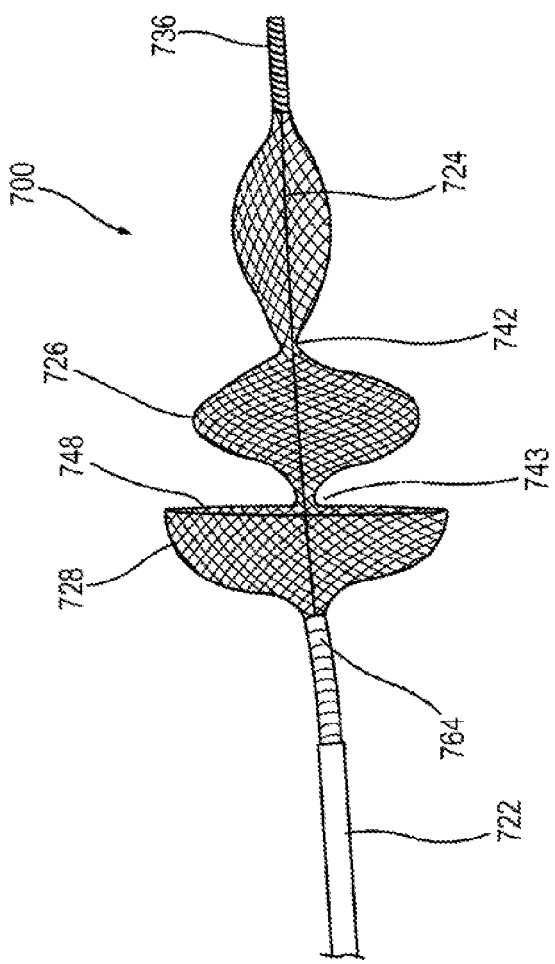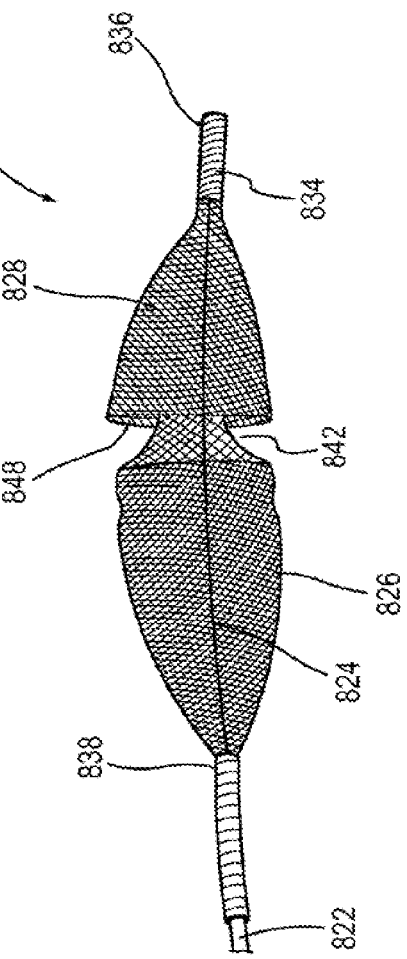

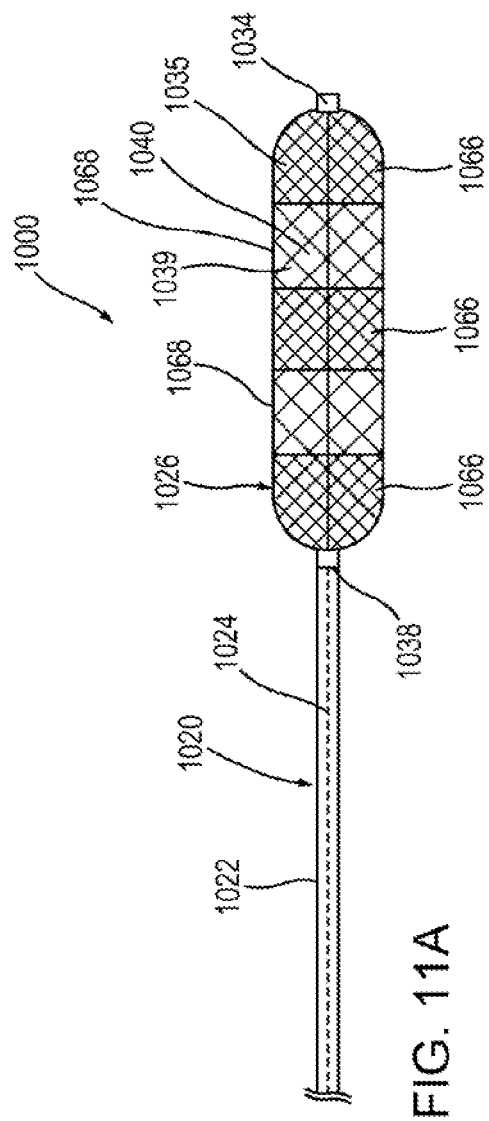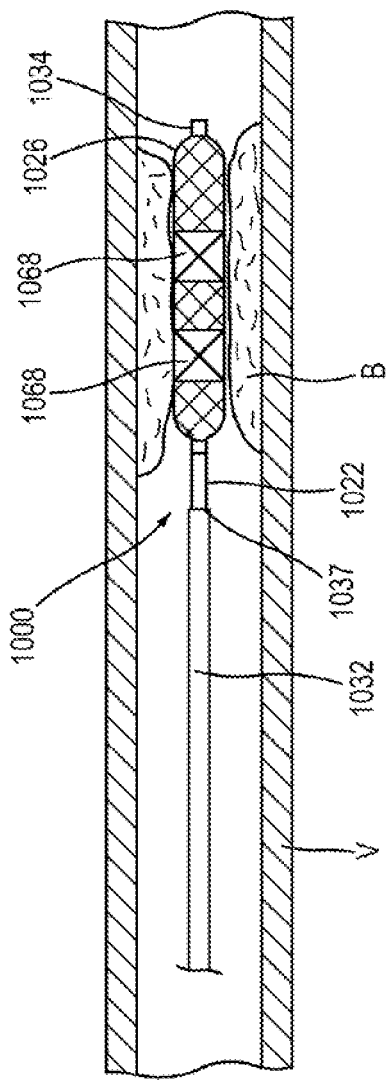

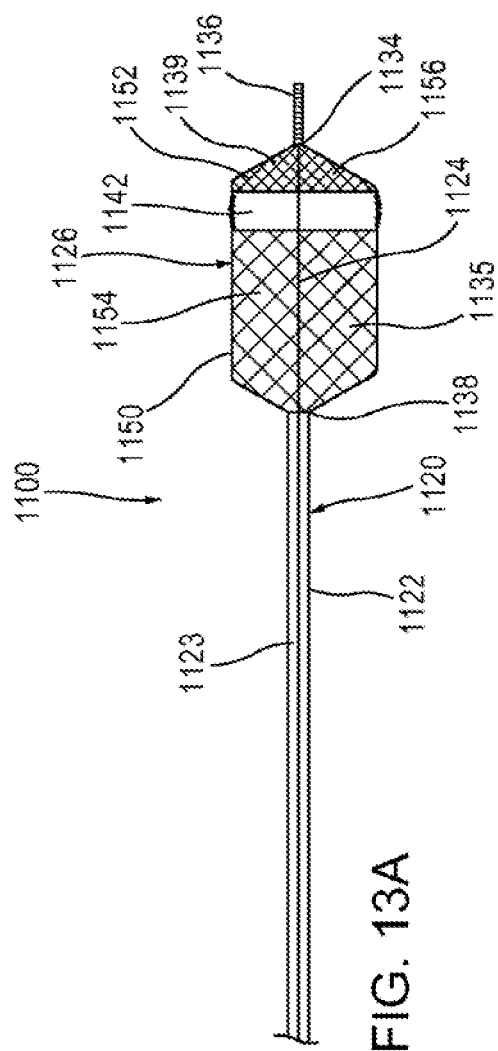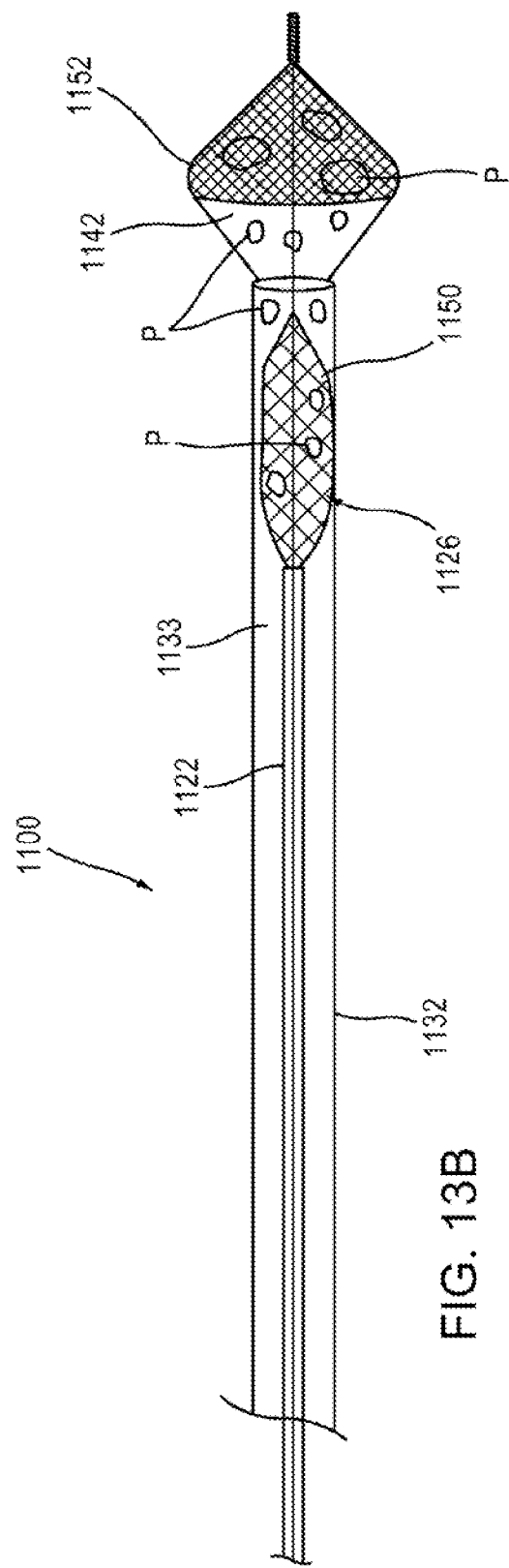

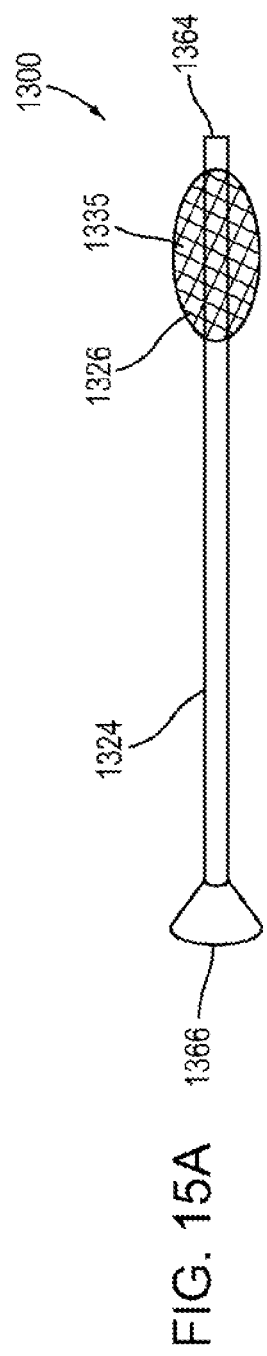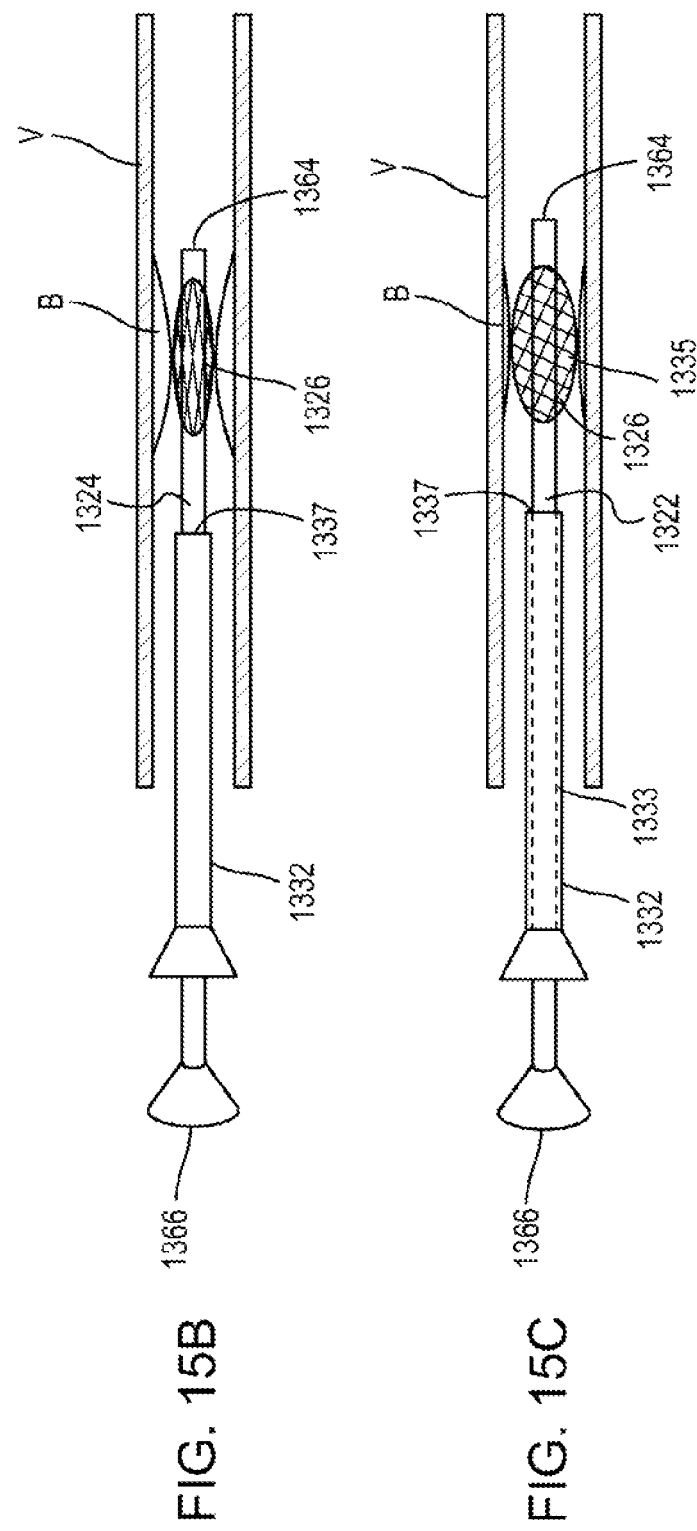
FIG. 15A    FIG. 15B    FIG. 15C

DEVICES AND METHODS FOR VASCULAR RECANALIZATION

CROSS-REFERENCES TO RELATED APPLICATIONS

This application is a continuation that claims priority to and the benefit of U.S. patent application Ser. No. 13/033, 100, entitled "Devices and Methods for Vascular Recanalization," filed Feb. 23, 2011, which claims priority to and the benefit of U.S. Provisional Patent Application No. 61/306, 951, entitled "Systems, Devices and Methods for Revascularization," filed Feb. 23, 2010, the disclosures of which are hereby incorporated by reference herein in their entirety.

BACKGROUND

The invention relates generally to medical devices and more particularly to expandable medical devices and methods for increasing blood flow through an obstructed blood vessel.

Some known medical devices used for increasing blood flow through an obstructed blood vessel include a filter trap designed and built to trap emboli. Such filters tend to be cumbersome and difficult to deploy. In addition, in some such devices, if the device is not properly seated in the vessel, the device can drift within the vessel. Some such devices are generally designed to catch emboli greater than a particular size (limited by the aperture size of the device walls), and are therefore not effective for removing smaller embolic particles.

In one known filter device, a basket is carried on a mandrel, which can be deployed and retracted through a catheter. In another known device, a vascular filter is collapsible, and includes a radially expandable body and proximal and distal sliders on a mandrel. The medical device can be used to filter fluid, but has the disadvantage of independent proximal and distal motion control, making it difficult to coordinate precisely and predictably a desired movement. Even if the filter trap effectively captures dislodged material within a vessel, retracting the filter trap into the catheter through which it was delivered can be difficult. Some known devices use vascular suction to suction or pull blood and clots out of the vessel.

Currently, few FDA-approved treatment options exist for an acute ischemic stroke. One option is an intravenous (IV) delivery of Tissue Plasminogen Activator (t-PA) (Activase), which is a thrombolytic agent. The agent is designed to dissolve the blood clot that is blocking blood flow to the brain. IV t-PA is currently limited in use because it must be used within a three hour window from the onset of a stroke and can result in an increased risk of bleeding. The second option is a thromboembolectomy device. The device is designed to capture an embolus or clot and remove it from the blocked vessel, thereby restoring blood flow. The device includes a cork-screwed guidewire, but is only able to capture and remove matter that is firm or held together by itself. In most cases, the device is used in combination with drug therapy to restore blood flow. A typical procedure using the device can take 2-3 hours to restore blood flow, if at all, and may take multiple passes through the vessel to either capture, macerate or open the vessel. In some cases, the device may capture an embolus, but then lose grasp of it and deposit it incidentally in another area of the neurovasculature, creating the potential for a new stroke in a new territory. In some cases, complications such as vessel dissection, perforation and hemorrhage arise as a result of over-manipulation in the vessel.

Thus, there is a need for improved systems, devices and methods for increasing blood flow through a blood vessel as described herein.

SUMMARY OF THE INVENTION

Devices and methods for increasing blood flow through a blood vessel are described herein. In one embodiment, an apparatus includes an elongate member and an expandable member coupled to a distal portion of the elongate member. The expandable member is configured to be inserted into a blood vessel and defines multiple openings in a wall of the expandable member. The expandable member has a collapsed configuration for insertion into the blood vessel and an expanded configuration in which the expandable member defines an interior volume in fluid communication with the multiple openings and is configured to receive therein at least a first portion of a bodily tissue. The expandable member includes a first portion having a first outer perimeter, a second portion having a second outer perimeter and a third portion having a third outer perimeter. The second outer perimeter is smaller than the first outer perimeter and smaller than the third outer perimeter such that the expandable member defines a capture region between the first portion and the third portion configured to receive at least a second portion of the bodily tissue.

BRIEF DESCRIPTION OF THE DRAWINGS

FIG. 2A is a side view of a medical device, according to an embodiment, shown disposed within a blood vessel and in a partially expanded configuration.

FIG. 2B is a side view of the medical device of FIG. 2A, shown in a first expanded configuration within a blood vessel.

FIG. 2C is a side view of the medical device of FIG. 2A, shown in a second expanded configuration within a blood vessel.

FIG. 2D is a cross-sectional view of a portion of the medical device of FIG. 2A, taken along line 2D-2D in FIG. 2A.

FIG. 8 is a side view of a portion of a medical device, according to another embodiment, shown in an expanded configuration.

FIG. 9 is a side view of a portion of a medical device, according to another embodiment, shown in an expanded configuration.

FIG. 11A is a side view of a medical device according to another embodiment, shown in an expanded configuration.

FIG. 11B is a side view of the medical device of FIG. 11A shown in a partially expanded configuration and disposed within a blood vessel.

FIG. 13A is a side view of a medical device according to another embodiment, shown in an expanded configuration.

FIG. 13B is a side view of the medical device of FIG. 13A, shown partially collapsed within a delivery catheter.

FIG. 15A is a side view of a medical device according to another embodiment, shown in an expanded configuration.

FIG. 15B is a side view of the medical device of FIG. 15A, shown in a partially expanded configuration disposed within a blood vessel adjacent a blockage.

FIG. 15C is a side view of the medical device of FIG. 15A, shown in an expanded configuration disposed within a blood vessel adjacent a blockage.

DETAILED DESCRIPTION

Figure 1:
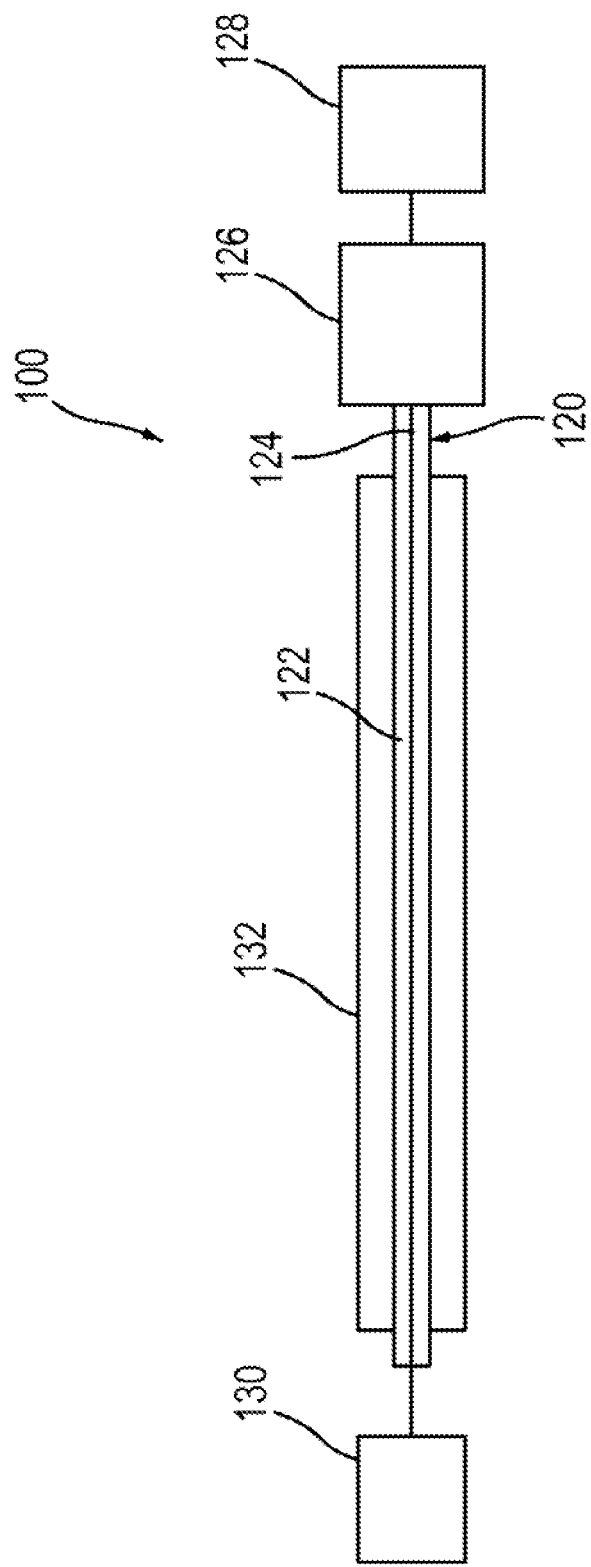
FIG. 1 is a schematic illustration of a medical device, according to an embodiment.

Medical devices and methods of treatment are described herein to treat patients experiencing a blockage in a circulatory blood vessel and the effects of that event, including ischemic stroke and/or heart attack. In some embodiments, a delivery apparatus, such as for example, a delivery catheter, is included for delivering a medical device to a treatment site within a patient. The medical devices and methods of treatment described herein can reduce ischemic events while recanalizing a vessel. In some embodiments, methods for retrieving and removing an obstruction responsible for a blockage before the vessel is re-opened are described and, in some cases, providing oxygenated blood or superoxygenated blood distal of the blockage while the obstruction is being cleared.

Various embodiments of a vascular recanalization device for recanalizing a blocked vessel are described herein. The vascular recanalization device (also referred to herein as "recanalization device" or "medical device") can include an elongate member having a hypotube and a core wire movably disposed therethrough, and an expandable member formed with, for example, woven or braided filaments in a mesh-like configuration. The terms mesh and braid can each refer herein to a fabric or material of woven or braided filaments or strands of wire or polymer. The expandable member of the recanalization device can be configured to compress or collapse for delivery into a blood vessel. In some embodiments, the recanalization device can be inserted while in a collapsed configuration through a delivery device, such as, for example, a microcatheter, delivery tube or sheath. In some embodiments, the recanalization device can be deployed without the use of such a delivery device.

The expandable member of the recanalization device can have a collapsed or compressed configuration such that the expandable member has a diameter that can fit within the narrow constraints of the neurovasculature and/or within a lumen of a delivery catheter. The expandable member of the recanalization device can be formed with, for example, an arrangement of strands (e.g., a mesh or braid arrangement of strands or filaments) that can compress and expand. The expandable member can be compressed over and/or along the elongate core wire of the recanalization device.

In some embodiments, a recanalization device includes a core wire movably disposed within a lumen of a hypotube. A distal portion of an expandable member (e.g., having mesh or braid) is attached to the core wire, and a proximal portion of the expandable member is attached to the hypotube. The expandable member can be moved from a collapsed configuration to an expanded configuration while disposed within a blood vessel. Control of the expansion of the expandable member can be achieved by axial adjustment of the relative positions of the hypotube and core wire, and by moving the hypotube or core wire relative to one another radially as described in more detail herein. When the expandable member expands, it can assume a structure that defines an interior volume through which the core wire extends. When disposed within a vasculature, as the expandable member expands, the expanded portion of the expandable member can exert a radial force such that the expanded portion can displace material in the vasculature or at the vascular wall.

While expanded, the expandable member can also be configured to be moved or contorted to alter the contour of its external surface. In some embodiments, contortion of the expanded expandable member can be actuated by twisting or rotating the hypotube and core wire in opposite directions (radial motion) to one another, or either the hypotube or the core wire can be twisted or rotated relative to the other while the other is maintained substantially stationary. The changed contour of the expandable member can include, for example, helical shelves that spiral along a length of the core wire. The spiral shelves can have spiral edges that can be used to carve, cut, shear or otherwise disrupt material in the vasculature to dislodge and capture the material. Compression of the expandable member can be actuated by opposite manipulations as described for the expansion process. In some embodiments, the contoured form of the expandable member can define capture spaces or regions. In some embodiments, capture spaces or regions can be pre-formed on an external surface of the expandable member. For example, in some embodiments, the expandable member can be formed with filaments of superelastic or shape memory material (such as, e.g., nitinol alloy) and the braid or mesh can be set in a predefined shape prior to attaching the expandable member to the elongate member of the recanalization device. In such an embodiment, when the expandable member expands, it assumes a biased predetermined shape.

The recanalization devices described herein can include one or more expandable members formed with a woven mesh or braid that has variably sized apertures that allow various sized portions or pieces of material (e.g., bodily tissue) to pass through the braid wall and to rest within an interior volume defined by the expandable member when expanded. In some embodiments, an expandable member can be a fabric of mesh or braid formed with wires having different diameters.

In some embodiments, an expandable member can have sections of mesh or braid having variation in density of the filaments and may include bands of dense filaments spaced by bands that are less dense. The less dense braid portion can have larger openings in the braid to capture dislodged material from a blockage. Material (e.g., bodily tissue such as a portion of a blood clot) can be encouraged to enter interstices of the mesh of the expandable member and when the expandable member is compressed or collapsed it can carry out dislodged material from the patient's body. The sections of the expandable member having larger openings (e.g., less dense sections) can also provide openings for larger pieces of material to pass into the expandable member. Thus, the expandable member (also referred to herein as "capture sack" or "capture bag") can capture material from a blocked vessel by encouraging the material to enter an interior region within the expandable member. The less dense sections can also direct the final shape of the expandable member. For example, sections of less dense (more open) mesh or braid can direct the effects of twisting so the less dense areas of braid contract with the twisting, and the more dense areas of braid form the helical shelves of a spiral shape. In some embodiments, material can also be captured within external folds formed on the exterior contour of the expanded member as described in more detail herein.

A recanalization device described herein can include an expandable member coupled at a proximal end to a tubular member, such as a hypotube, and at a distal end to an elongate member (also referred to herein as a "core wire") that can be movably disposed within a lumen of the tubular member. In some embodiments, the expandable member can include an increasing radial expansion and radial force on the proximal end of the expandable member where it is coupled to the hypotube. To move the expandable member from a first configuration to a second configuration, the hypotube can be pushed and the elongate member pulled to create axial shortening and radial expansion. Other manipulations by the practitioner using a controller or actuator disposed at a proximal end of the expandable medical device (usually external of the body of the patient) are also possible.

In some embodiments, a recanalization device can be delivered to a desired treatment site within a vasculature by inserting the expandable medical device through a lumen of a delivery catheter (e.g., a microcatheter). The expandable medical device can be inserted through the delivery catheter in a collapsed or compressed configuration. The expandable member of the expandable medical device can be moved out through a distal end of the delivery catheter at the treatment site (e.g., adjacent to or within a blood clot) and moved to an expanded configuration. In some embodiments, the delivery catheter is used to compress or collapse the expandable member. For example, the expandable member can be formed with a biased expanded configuration and when it is placed within a lumen of a catheter it is compressed. When the expandable member is moved outside of the catheter, it can assume its biased expanded configuration.

In some embodiments, a recanalization device can be used without a delivery catheter. For example, in some embodiments, a recanalization device can include an elongate member or wire having an integral expandable section that can be controlled by the proximal end of the wire. For example, the wire can be pushed relative to the tubular member to compress the expandable section and pulled to expand it. A control unit at the proximal end of the medical device can be used to push the elongate member to maintain closure and compress the mesh or braid, and to pull the elongate member to expand the mesh or braid once the unit is at the blockage. In addition, the elongate member can be rotated such that the expandable member is rotated at the blockage and provides abrasion for scraping or loosening blockage material. Because the expandable member is easily manipulated between configurations from a location outside the body, the expandable member can be actuated between various configurations without a microcatheter. In such an embodiment, the expandable member and elongate member can have a greater outer diameter (i.e. denser braid, or thicker filaments) if desired.

In some embodiments, a recanalization device can include a first expandable member formed with mesh or braid and defining an interior region when moved to an expanded configuration, and a second expandable member that can have a substantially parabolic shape configured to capture vascular material as the expandable medical device is pulled through the vessel. The second expandable member can also be referred to herein as a "cap" or "catch basket." In some embodiments, the second expandable medical can be disposed distal of the first expandable member and can be used to capture dislodged material flowing downstream of the first expandable member. In some embodiments, the second expandable medical can be disposed proximal of the first expandable member and can be used to capture dislodged material moving upstream of the first expandable member.

In some embodiments, the second expandable member can be formed integrally or monolithically with the first expandable member and include, for example, wires or threads connecting the second expandable member to the first expandable member at a non-zero or spaced distance from the first expandable member. In some embodiments, the second expandable member can be woven or braided using the same filaments that form the first expandable member. To create a separation or opening between the cap and the body, the filaments from the weave or braid of the second expandable member (e.g., cap) are condensed (i.e., tied off) in one or more bundles that serve as legs separating the two expandable members, and the filaments can be organized in a continuation of a weaving pattern to form the first expandable member. In some embodiments, movement of the second expandable member (e.g., cap) between a closed or collapsed configuration and an expanded or open configuration can be controlled with wires that lead from the second expandable member to a distal end of the device.

In some embodiments, the capture cap or basket can be formed on the bias of woven mesh or braid so that the capture cap closes and removes into the catheter more easily. For example, a cinch tie along the bias (slant) of the braid can be less bulky for reentry into the microcatheter and the braid ends can be more responsive to the action of cinching on the bias of the woven filaments. Such an embodiment is described in more detail herein. In some embodiments, a core wire can be coupled to the capture cap and used to hold and control the opening and closure of the capture cap.

In some embodiments, an expandable medical device includes an elongate member that defines a longitudinal axis and an expandable member is coupled to a distal portion of the elongate member. The expandable member is configured to be inserted into a blood vessel and defines multiple openings in a wall of the expandable member. The expandable member defines a proximal opening larger than the multiple openings in the wall of the expandable member. The proximal opening is defined at an angle transverse to the longitudinal axis of the elongate member. The expandable member has a collapsed configuration for insertion into the blood vessel and an expanded configuration. When in the expanded configuration, the expandable member defines an interior volume in fluid communication with the multiple openings. The expandable member when in the expanded configuration is configured to capture portions of a bodily tissue within the interior region of the expandable member and to prevent portions of the bodily tissue from migrating within the blood vessel past the expandable member. The expandable member is configured to be moved to the collapsed configuration while disposed within the blood vessel such that the proximal opening is at least partially closed and the captured portions of the bodily tissue are trapped within the interior region.

In one method of using a vascular recanalization device, super-oxygenated blood or oxygenated blood can be perfused distal of a blockage within a vasculature to reduce or eliminate ischemia during the procedure by providing the region cut off by blood supply fresh oxygenated blood to keep the tissue alive.

Methods of unblocking a vessel, removing a clot, and treating patients having blockages are described herein. In some embodiments, a method of restoring blood flow in a blocked vessel can include inserting an expandable member of a recanalization device within a lumen of a delivery sheath or catheter such that the expandable member is compressed or collapsed. A distal end portion of the sheath can be positioned at a desired treatment site, for example, near a blockage (e.g., blood clot) in a blocked vessel. The sheath can be moved proximally or the expandable medical device can be moved distally, such that the expandable member is moved outside a distal end of the sheath, thereby releasing the restraint on the expandable member and allowing it to move to an expanded configuration. As the expandable member moves to the expanded configuration, the expandable member can contact material in the blockage. In some embodiments, as the expandable member expands and contacts the material in the blockage, it mechanically induces a shape change in the expandable member to optimize contact with the material and effect displacement of material forming the blockage.

In some embodiments, a method can further include capturing material dislodged from the blockage; removing the captured material; and perfusing a region distal of the blockage with oxygenated blood during the blood flow restoration procedure. In some embodiments, the expandable member is in the form of a braided tube that includes fibers of a super elastic shape memory alloy, or polymeric fibers. In some embodiments, the expandable member can effect a shape deformation inducing a helical contour along a longitudinal axis of the expandable member. In some embodiments, the shape deformation can include inducing radial expansion and axial shortening. In some embodiments, a distal end of the expandable member can be attached to a guidewire and a proximal end of the expandable member can be attached to a hypotube through which the guidewire passes and inducing a shape change can be accomplished by rotating the guidewire and/or the hypotube radially in opposite directions.

In some embodiments, a recanalization device can include an expandable member (e.g., a braided or mesh component) attached at a distal end to a guide wire and at a proximal end to a hypotube through which the guide wire passes. The expandable member can be adapted to plastically deform for compression when disposed within a lumen of a catheter for delivery, and to expand upon removal of the catheter. The expanded expandable member can be capable of changing shape by mechanical manipulation of the guide wire and/or the hypotube. In some embodiments, the expandable member can include a variable density braid, and be closed at a distal end and open at a proximal end such that material (e.g., bodily tissue) can be collected therethrough. In some embodiments, the expandable member can have two layers of braid and can have a changed shape adapted to capture material. In some embodiments, the changed shape can include radial expansion or axial shortening or both. In some embodiments, the expandable member can have interstices adapted to capture material. In some embodiments, the filaments forming the expandable member can include, for example, super elastic metal alloy, polymeric fiber, and/or drawn filled tube (DFT) radiopaque wire. In some embodiments, the expandable member can have a changed shape that includes a helical contour on an outside surface of the expandable member. In some embodiments, the expandable member can include interwoven polymeric fibers and super elastic alloy wire.

In some embodiments, a recanalization device can include a capture cap at a distal end of the device that can have braided fibers clipped on a bias at the proximal opening of the cap forming an elliptical shape at the opening. The cap can thereby be adapted for cinching closed at the elliptical opening. Such a medical device can have a reduced diameter upon radial compression compared to a device made by clipping the braided fibers of the capture cap on a radial axis forming a circular opening.

In some embodiments, a recanalization device as described herein can be used for delivering oxygenated blood to a region in the brain during a procedure to remove a blockage in a vessel. A method of recanalization of a blocked vessel can include, for example, positioning an expandable mesh member affixed at a distal end to a delivery wire at a site of a blockage in a vessel. The expandable mesh member can be expanded at the blockage location. The expandable mesh member can be moved to a contoured shape (while expanded) by twisting the delivery wire counterclockwise or clockwise. Material from the blockage can be captured within contour variations of the outer mesh surface.

In some embodiments, a method of recanalization of a blocked vessel includes positioning a tubular-shaped expandable mesh member affixed at a distal end to a delivery wire at a site of blockage in a vessel. The expandable mesh member can have a predefined variable contour on an outer surface and a distal mesh capture bag. The distal mesh capture bag can include a cinch on a diagonal wire of the mesh. The expandable mesh member and the distal mesh capture bag can be expanded such that material from the blockage that flows distal of the expandable mesh member can be captured within the capture bag. The capture bag can be compressed or closed by cinching the bag, and the expandable mesh member and the capture bag can be removed from the vessel.

The recanalization devices described herein can be used to unblock vessels to allow the resumption of blood flow during events, such as, for example, ischemic stroke. In some embodiments, wire or polymer filaments can be used to form a woven mesh or braided strands that can be expandable, and have apertures sized to capture material disrupted by expansion of the device at a blockage site (e.g., a blood clot). The recanalization devices can be configured for axial compression and radial expansion. The expandable member of the recanalization device can be configured to have sufficient radial force to expand through material blocking the vessel and masticate or disrupt the material with the wires of the mesh or braid. The expandable member when expanded includes a capture structure that defines an interior region. The capture structure includes interstices in the mesh or braid through which the material from the blockage can pass and be retained within the interior region of the expanded expandable member. The expandable member can also include an external contour for capturing material in capture spaces or regions defined by the expanded expandable member while disposed within the vessel. In some embodiments, the recanalization device can also have a capture bag disposed distal to the expandable member that can be used to catch pieces of material that flow distally from the blockage. In some embodiments, the recanalization device can include a capture bag disposed proximally to the expandable member. The recanalization device can be retrievable and can remove material captured within the expandable member when it is compressed or collapsed for removal from the vessel. The recanalization device can be used with or without a microcatheter or sheath for delivery of the recanalization device to a treatment site within a vessel.

In some embodiments, a recanalization device can include a mesh expandable member coupled to an elongate member that includes a hypotube and a core wire movable disposed within a lumen of the hypotube. The expandable member can have a distal attachment to the core wire, and a proximal attachment to the hypotube. The expandable member can be delivered to a treatment site within a vessel by being passed through a lumen of a delivery catheter or sheath while in a compressed or collapsed configuration and moved through the vessel-obstructing material. Upon withdrawal of the catheter or sheath, the mesh expandable member expands to an open or expanded configuration that is capable of contacting material that forms the blockage. Further and more complete vessel clearance can be achieved by rotating the hypotube and wire in opposite directions (radially), which causes the expanded expandable member to contract at distinct intervals. This creates pockets of capture space on an external contour of the device. In some embodiments, the region downstream of the blockage can be accessed with a perfusion catheter or like device and perfused with oxygenated or superoxygenated blood for the duration of the recanalization procedure to reduce or avoid ischemic damage. Material from the blockage can be captured within an interior region of the expandable member through interstices of the mesh or braid of the expandable member, or the material can be captured in the capture spaces defined along the external contour of the expandable member. Material captured within the capture spaces or within the interior region of the expandable member, can be pulled back into the catheter or sheath for removal from the patient.

It is noted that, as used in this written description and the appended claims, the singular forms "a," "an" and "the" include plural referents unless the context clearly dictates otherwise. Thus, for example, the term "a lumen" is intended to mean a single lumen or a combination of lumens. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, the end inserted inside a patient's body would be the distal end of the medical device, while the end outside a patient's body would be the proximal end of the medical device.

FIG. 1 is a schematic illustration of a vascular recanalization device according to an embodiment. A vascular recanalization device 100 (also referred to herein as "recanalization device" or "medical device") can include a first expandable member 126 and an optional second expandable member 128 each coupled to an actuation member 120. The actuation member 120 can include a tubular member 122 that defines a lumen and an elongate member 124 movably disposed within the lumen of the tubular member 122. The tubular member 122 can be, for example, a hypotube, and the elongate member 124 can be, for example, a core wire. The actuation member 120 can optionally be coupled on a proximal end portion to a controller device 130, such as, for example, a hand-held controller. The recanalization device 100 can be used with a catheter or sheath 132 to, for example, deliver a distal portion of the recanalization device 100 to a treatment site within a vessel, as described in more detail herein.

The elongate member 124 can include a distal end portion configured to be inserted into a vessel and passed through a blockage (e.g., blood clot) at a target treatment site. In some embodiments, the distal end portion has a blunt distal end such that it does not damage the vessel when being inserted therein. In some embodiments, the distal end portion of the elongate member 124 can be coiled. The controller device 130 can be used to actuate movement of the elongate member 124 and/or the tubular member 122. In some embodiments, the elongate member 124 and the tubular member 122 can be manually manipulated without the use of a controller device 130. For example, a user (e.g., physician) can move or maneuver the tubular member 122 and the elongate member 124 by maneuvering a proximal end portion of the elongate member 124 and a proximal end portion of the tubular member 122. For example, in some embodiments, depending on the configuration, the elongate member 124 is moved for and aft (e.g., longitudinally) relative to the tubular member 122. In some embodiments, one or both of the tubular member 122 and the elongate member 124 can be rotated.

In some embodiments, the elongate member 124 can define a lumen extending between a proximal end portion and a distal end portion. The lumen can be used to inject or perfuse an oxygenated or superoxygenated blood into a blood vessel downstream of a blockage. For example, the recanalization device 100 can be inserted through a blockage such that a distal end of the elongate member 122 extends beyond or distal of the blockage. Oxygenated or superoxygenated blood can be injected into the blood vessel while the blockage is being disrupted or cleared during a recanalization procedure.

A distal portion of the first expandable member 126 can be coupled to a distal portion of the elongate member 124, and a proximal portion of the first expandable member 126 can be coupled to a distal portion of the tubular member 122. The second expandable member 128 can be coupled to the elongate member 124. In some embodiments, the second expandable member 128 can also include a cinch cord (not shown) extending from the second expandable member 128 and outside of the patient that can be used to open and close the second expandable member 128 as described in more detail below.

The first expandable member 126 can be formed with a mesh or braided material such that a wall of the first expandable member 126 defines multiple openings or interstices. The first expandable member 126 can have a collapsed or compressed configuration and an expanded configuration. When in the collapsed configuration, the first expandable member 126 has a smaller outer perimeter or outer diameter than when in the expanded configuration. The first expandable member 126 when in the first expanded configuration defines an interior region in fluid communication with the multiple openings or interstices defined in the wall of the first expandable member 126. In some embodiments, the first expandable member 126 can define more than one interior region or can include an interior region having multiple chambers.

In some embodiments, the first expandable member 126 can be formed with a shape-memory material, such as, for example, Nitinol, and can be preformed to assume a desired shape. Thus, in such an embodiment, the first expandable member 126 can be biased into an expanded configuration and moved to a collapsed configuration by restraining or compressing the first expandable member 126. In some embodiments, the first expandable member 126 can be configured to be mechanically actuated to move between a collapsed configuration and an expanded configuration. For example, the controller device 130 can be configured to move or actuate the first expandable member 126 between a collapsed configuration for insertion into a body lumen and/or a catheter, and an expanded configuration for use during a recanalization procedure.

The first expandable member 126 when in the expanded configuration can have a variety of different shapes, sizes and configurations. For example, in some embodiments, when the first expandable member 126 can be substantially tubular shaped. In some embodiments, the first expandable member 126 can have a substantially constant outer diameter or outer perimeter along a length of the first expandable member 126. In some embodiments, the first expandable member 126 can include multiple portions having varying outer perimeters or outer diameters. For example, in some embodiments, the first expandable member 126 can include a first portion having a first outer perimeter, a second portion having a second outer perimeter and a third portion having a third outer perimeter. In such an embodiment, the second outer perimeter can be smaller than the first outer perimeter and smaller than the third outer perimeter such that the first expandable member defines a capture space or region between the first portion and the third portion. A "capture region" as described herein can be a void, space or region defined in part by the first expandable member 126 and in which a portion or portions of bodily tissue (e.g., a portion of a blood clot) can be disposed, as described in more detail below. The first expandable member 126 can be configured with one or more capture regions. In some embodiments, the first expandable member 126 can be preformed with a portion or portions defining one or more capture regions. In some embodiments, the first expandable member 126 can be moved to a configuration in which the first expandable member 126 defines one or more capture regions as described below.

In some embodiments, the first expandable member 126 can have a compressed or collapsed configuration, a first expanded configuration and a second expanded configuration. For example, the first expandable member 126 can be inserted into a body lumen such as a blood vessel while in the collapsed configuration and moved to the first expanded configuration at a treatment site within the body lumen. While in the first expanded configuration, the first expandable member 126 can be moved to a second expanded configuration in which the first expandable member 126 changes shape. For example, the first expandable member 126 can be twisted such that the first expandable member 126 has a contoured outer exterior surface. In the second expanded configuration, the first expandable member 126 can define one or more capture regions as described herein.

The second expandable member 128 can be configured to the same as, or similar to the first expandable member 126. For example, the second expandable member 128 can be formed with a mesh or braided material such that a wall of the second expandable member 128 defines multiple openings or interstices. The second expandable member 128 can have a collapsed or compressed configuration and an expanded configuration. When in the collapsed configuration, the second expandable member 128 has a smaller outer perimeter or outer diameter than when in the expanded configuration. The second expandable member 128 when in the expanded configuration can define one or more interior regions in fluid communication with the multiple openings or interstices defined in the wall of the expandable member 128. The second expandable member 126 can be formed with a shape memory material such that it has a biased expanded configuration, or can be configured to be actuated with, for example, the controller device 130, between its collapsed configuration and an expanded configuration.

The second expandable member 128 can have a variety of different shapes, sizes and configurations when in the expanded configuration. The second expandable member can be the same as, or similar to, the first expandable member 126. In some embodiments, the second expandable member 128 can be formed such that when in the expanded configuration the second expandable member 128 can define a capture opening that is larger than the multiple openings or interstices defined in the wall of the second expandable member 128. In some embodiments, the second expandable member 128 can form a cup or parabolic shape. The capture opening can be opened or closed with a cinch member, such as, a wire or cord coupled to the second expandable member 128. In some embodiments, the capture opening can be defined on a bias or angled relative to a longitudinal axis of the recanalization device 100. In such an embodiment, the angled capture opening can facilitate delivery and withdrawal of the recanalization device 100 from a blood vessel due to a reduced mass or bulk of the second expandable member 128. The second expandable member 128 can be disposed proximal or distal to the first expandable member 126. In some embodiments, the second expandable member 128 can have a helical configuration when in the expanded configuration. In some embodiments, the second expandable member 128 can be substantially triangular shaped in a side view.

In one example use of the recanalization device 100, a catheter 132 can be inserted into a blood vessel and directed to a desired treatment site near a blockage, such as, a blood clot. In this example, the recanalization device 100 does not include a second expandable member 128. The recanalization device 100 can be inserted through the catheter 132 in a compressed or collapsed configuration and moved outside through a distal end of the catheter 132 such that the first expandable member 126 is positioned within a portion of the blockage. As the first expandable member 126 is moved outside of the catheter 132, it can assume a biased expandable configuration or otherwise be actuated to move to its expanded configuration such that the walls of the first expandable member 126 contact at least a portion of the blockage. The force of the first expandable member 126 contacting the blockage can cause a portion or portions of the blockage to pass through the openings in the wall of the first expandable member 126 and be disposed within the interior region of the first expandable member 126. The first expandable member 126 can optionally be rotating while expanded and disposed within the blockage such that further disruption of the blockage can occur and additional portions of the blockage can enter the first expandable member 126. In some embodiments, the first expandable member 126 can also optionally be moved to a contoured configuration while expanded. For example, the elongate member 124 and/or the tubular member 122 can be rotated such that the first expandable member is twisted into a contoured (e.g., helical) shape. The twisted, contoured shape can define capture regions in which portions of the blockage can be disposed. When the process of breaking up or disrupting the blockage is completed, the first expandable member 126 can be moved to its collapsed configuration by either pulling the first expandable member 126 back into the distal end of the catheter 132, or by actuating the first expandable member 126 to move to its collapsed configuration depending on the particular configuration of the first expandable member 126.

FIGS. 2A-2D illustrate another embodiment of a recanalization device. A recanalization device 200 (also referred to herein as "recanalization device" or "medical device") includes an expandable member 226 coupled to an actuation member 220. The actuation member 220 includes a tubular member 222 that defines a lumen 223 (see e.g., FIG. 2D) between a proximal end and a distal end of the tubular member 222, and an elongate member 224 movably disposed within the lumen 223 of the tubular member 222. The tubular member 222 can be, for example, a hypotube, and the elongate member 124 can be, for example, a core wire. The actuation member 220 can optionally be coupled on a proximal end portion to a controller device (not shown), such as, for example, a hand-held controller as described above. The recanalization device 200 can be inserted through a lumen 233 (see e.g., FIG. 2D) of a catheter or sheath 232, which will compress the expandable member 226 into a collapsed or compressed configuration (not shown).

A proximal end portion of the expandable member 226 is coupled to a distal end portion 225 of the tubular member 222 at attachment 238, and a distal end portion of the expandable member 226 is coupled to a distal end portion 236 of the elongate member 224 at attachment 234. The expandable member 226 can be attached with, for example, a clamp, clip, bonding, heat sealed, weld, or other suitable coupling mechanism. The distal end portion 236 of elongate member 224 is coiled and extends distally of the expandable member 226 and can be used to penetrate through a blockage B (e.g., a blood clot) within a blood vessel V.

As described above for the previous embodiment, the expandable member 226 can be formed with a mesh or braided material such that a wall of the expandable member 226 defines multiple openings or interstices 235. The expandable member 226 can have a collapsed or compressed configuration (not shown) and an expanded configuration (see e.g., FIG. 2B). When in the collapsed configuration, the first expandable member 226 has a smaller outer perimeter or outer diameter than when in the expanded configuration. When in the expanded configuration, the expandable member 226 defines an interior region 240 (see e.g., FIG. 2B) in fluid communication with the multiple openings 235. The expandable member 226 can be formed with a shape-memory material such that it is biased into its expanded configuration when not restrained as shown in FIG. 2B and can be inserted into the lumen 233 of the catheter 232 to move to its compressed configuration.

In use, the catheter 232 can be inserted through a blood vessel V in a direction of the blood flow F and a distal end 237 of the catheter 232 can be positioned near a blockage B as shown in FIG. 2A. The expandable member 226 can be moved out the distal end 237 of the catheter 232 by moving the actuation member 220 (i.e., the tubular member 222 and the elongate member 224) distally through the blockage B where the expandable member 226 can begin to assume its biased expanded configuration as shown in FIG. 2A. As the expandable member 226 moves to its expanded configuration as shown in FIG. 2B, the expandable member 226 can contact and exert a force on the blockage B such that the blockage B is compressed and portions of the blockage B are moved through the openings 235 of the expandable member 226 and into the interior region 240 of the expandable member 226.

As described above, the expandable member 226 can optionally be rotated to further disrupt the blockage B. In addition, the expandable member 226 can be moved to a contoured or tortuous shape as shown in FIG. 2C. For example, the tubular member 222 and/or elongate member 222 can be rotated relative to the other, or both can be rotated in opposite directions such that expandable member 226 is twisted into a tortuous or helical configuration. As shown in FIG. 2C, the expandable member 226 defines capture regions 242 that can received dislodged or disrupted portions P of blockage B. When the disruption procedure is completed, the elongate member 224 can be pulled proximally such that the expandable member 226 partially collapses in a longitudinal direction (e.g., parallel with an axis defined by the blood vessel V) and the portions P are captured or trapped by the expandable member 226. The expandable member 226 can then be pulled proximally (e.g., by pulling the tubular member 222 and the elongate member 224) back into the lumen 233 of the catheter 232 with the trapped portions P of the blockage B and the portions of the blockage B captured within the interior region 240 of the expandable member 226.

Figure 3:
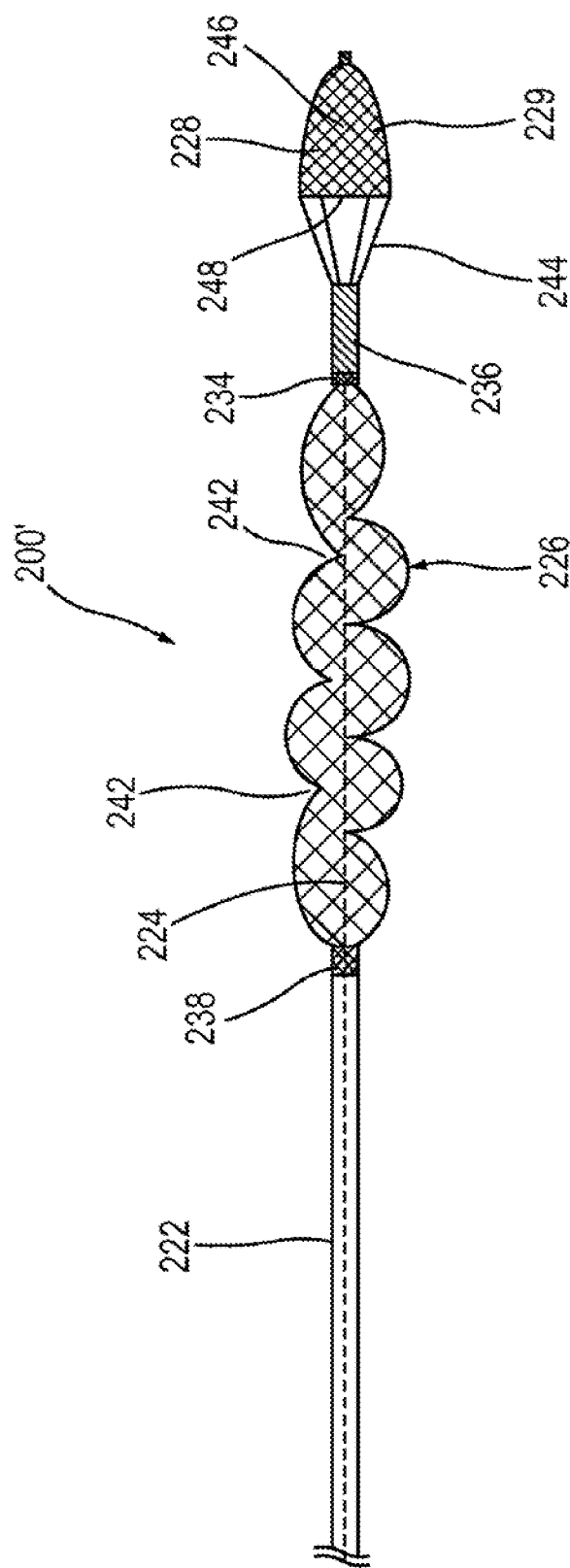
FIG. 3 is a side view of a medical device, according to an embodiment, shown in a contoured, expanded configuration.

FIG. 3 illustrates a variation of the recanalization device 200. A recanalization device 200' includes all the same features and functions as described above for recanalization device 200. For example, the recanalization device 200' includes an expandable member 226' coupled to a tubular member 222' at attachment 238' and coupled to an elongate member 224' at attachment 234'. The elongate member 224' includes a distal end portion 236'. The recanalization device 200' is shown in an expanded configuration and moved into a contoured or tortuous shape as described above and shown in FIG. 2C. In this embodiment, the recanalization device 200' includes a second expandable member 228 coupled to the distal end portion 236' of the elongate member 224'.

The second expandable member 228 is coupled to the elongate member 224' with wires or filaments 244. The second expandable member 228 is formed with a mesh or braided material that defines multiple openings 229. The second expandable member can be formed with a shape-memory material such that it is biased into an expanded or open configuration as shown in FIG. 3 and can be moved to a compressed or closed configuration in a similar manner as described above for expandable member 224. For example, when the recanalization device 200' is inserted into a lumen of a catheter (e.g., catheter 232) the second expandable member 228 can be compressed or collapsed.

When in its expanded configuration as shown in FIG. 3, the second expandable member 228 has a cup or parabolic shape and defines an interior region 246 in fluid communication with the openings 229. The second expandable member 228 also defines a proximal opening 248 that is in fluid communication with the interior region 246. Thus, the expandable member 228 is open at its proximal end facing the expandable member 226'. The second expandable member 228 can be used as a capture cap during a recanalization procedure. For example, during a recanalization procedure as described above for recanalization device 200, the expandable member 228 can be used to prevent dislodged or disrupted portions of the blockage from migrating beyond or distally of the expandable member 228 upstream within the blood vessel. Further, when the recanalization device 200' is moved proximally to remove the recanalization device 200' from the blood vessel, the second expandable member 228 can collect or capture portions of the disrupted blockage within its interior region.

Figure 4A:
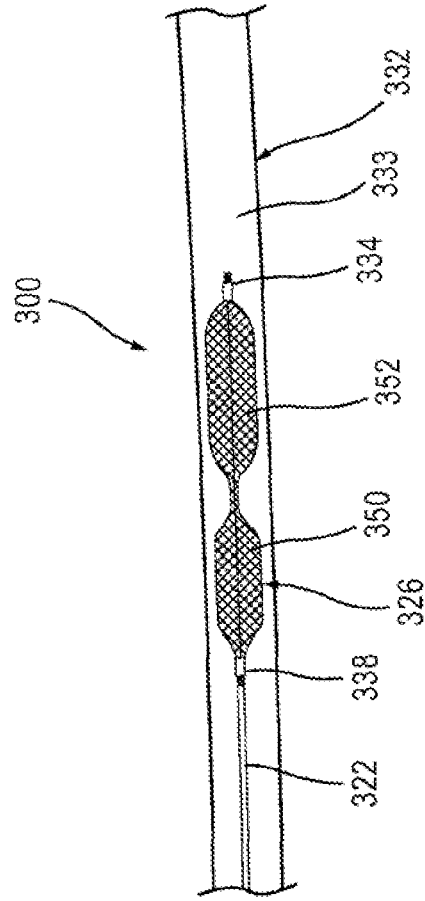
FIG. 4A is a side view of a medical device, according to an embodiment, shown in a collapsed configuration disposed within a catheter.
Figure 4B:
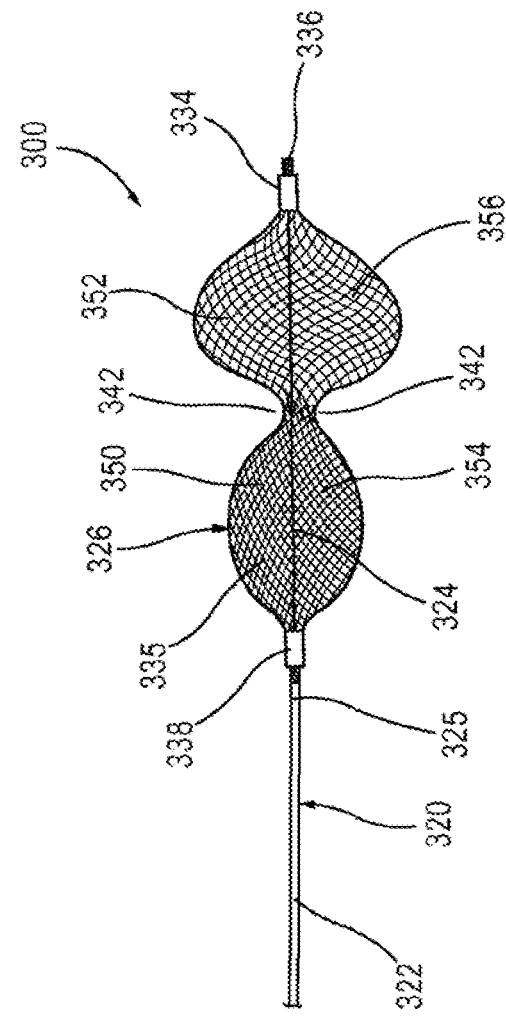
FIG. 4B is a side view of a portion of the medical device of FIG. 4A shown in an expanded configuration.

FIGS. 4A and 4B illustrate another embodiment of a recanalization device. A recanalization device 300 (also referred to herein as "recanalization device" or "medical device") includes an expandable member 326 coupled to an actuation member 320. The actuation member 320 includes a tubular member 322 that defines a lumen (not shown) between a proximal end and a distal end of the tubular member 322, and an elongate member 324 movably disposed within the lumen of the tubular member 322. The actuation member 320 can optionally be coupled on a proximal end portion to a controller device (not shown), such as, for example, a hand-held controller as described above. The recanalization device 300 can be inserted through a lumen not 333 of a catheter or sheath 332, which will compress the expandable member 326 into a collapsed or compressed configuration (as shown in FIG. 4A).

A proximal end portion of the expandable member 326 is coupled to a distal end portion 325 of the tubular member 322 at attachment 338, and a distal end portion of the expandable member 326 is coupled to a distal end portion 336 of the elongate member 324 at attachment 334. The expandable member 326 can be attached with, for example, a clamp, clip, bonding, heat sealed, or other suitable coupling mechanism.

The expandable member 326 can be formed with a shape-memory material and has a collapsed configuration (as shown in FIG. 4A) and a biased expanded configuration as shown in FIG. 4B. In this embodiment, the expandable member 326 has a preformed expanded configuration that defines a first portion 350 and a second portion 352 of the expandable member 326. The expandable member 326 can be formed with a mesh or braided material such that a wall of the expandable member 326 defines multiple openings or interstices 335. When in the collapsed configuration, the first portion 350 and the second portion 352 of the expandable member 326 each have a smaller outer perimeter or outer diameter (as shown in FIG. 4A) than when in the expanded configuration (as shown in FIG. 4B). When in the expanded configuration, the expandable member 326 defines a first interior region 354 associated with the first portion 350 and a second interior region 356 associated with the second portion 352. The first interior region 354 and the second interior region 356 are each in fluid communication with the openings 335. Also when in its expanded configuration, the expandable member 326 defines an annular capture region 342 between the first portion 350 and the second portion 352.

In some embodiments, the shape of the expandable member 326 can be further changed by pulling the elongate member 324 proximally and holding the tubular member 322 stationary, or moving the tubular member 322 distally and holding the elongate member stationary, or moving the elongate member 324 proximally while moving the tubular member 322 distally. Such action can cause the expandable member 324 to at least partially collapse in a longitudinal direction. In other words, the first portion 350 and the second portion 352 of the expandable member 326 can be moved closer to each other and the outer perimeter of the first portion 350 and the outer perimeter of the second portion 352 can be increased.

In use, the catheter 332 can be inserted through a blood vessel and a distal end (not shown) of the catheter 332 can be positioned near a blockage within the blood vessel. The expandable member 326 can be moved out the distal end of the catheter 332 by moving the actuation member 320 (i.e., the tubular member 322 and the elongate member 324) distally. As the expandable member 326 moves to its expanded configuration as shown in FIG. 4B, the expandable member 326 can contact and exert a force on the blockage such that the blockage is compressed and portions of the blockage are moved through the openings 335 of the expandable member 326 and into the interior regions 354 and 356. Portions of the blockage can also be captured within the capture region 342 in a similar manner as described above for recanalization device 200. As described above, the expandable member 326 can optionally be rotated to further disrupt the blockage.

When the disruption process is completed, the elongate member 324 can be pulled proximally such that the expandable member 326 partially collapses in a longitudinal direction (e.g., parallel with an axis defined by the blood vessel) and portions of bodily tissue within the capture region 342 can be captured or trapped by the expandable member 326. The expandable member 326 can then be pulled proximally (e.g., by pulling the tubular member 322 and the elongate member 324) back into the lumen 333 of the catheter 332 with the trapped portions of bodily tissue within the capture region 342 and the portions captured within the interior regions 354 and 356 of the expandable member 326.

Figure 5:
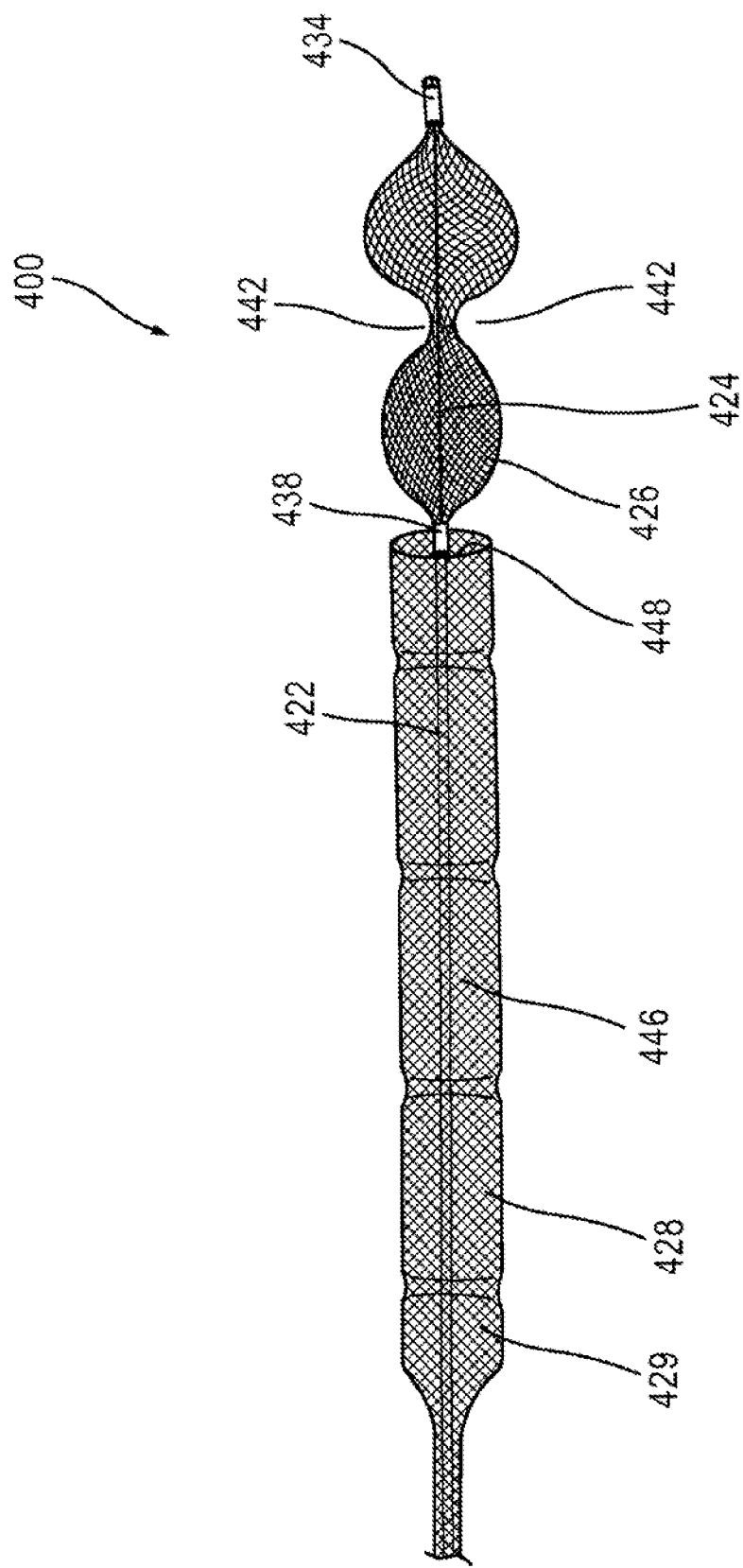
FIG. 5 is a side view of a portion of a medical device, according to another embodiment, shown in an expanded configuration.

FIG. 5 illustrates a variation of the recanalization device 300. A recanalization device 400 includes all the same features and functions as described above for recanalization device 300. For example, the recanalization device 400 includes an expandable member 426 coupled to a tubular member 422 at attachment 438 and coupled to an elongate member 424 at attachment 434. The recanalization device 400 is shown in an expanded configuration and can be moved between a compressed or collapsed configuration and the expanded configuration in the same or similar manner as described above for recanalization device 300. In this embodiment, the recanalization device 400 includes a second expandable member 428 coupled to the tubular member 422 proximal of the expandable member 426.

The second expandable member 428 can be formed with a mesh or braided material that defines multiple openings as described for expandable member 426. The second expandable member 428 can be formed with a shape-memory material such that it is biased into an expanded or open configuration as shown in FIG. 5, and can be moved to a compressed or closed configuration in a similar manner as described above for expandable member 326. For example, when the recanalization device 400 is inserted into a lumen of a catheter (e.g., catheter 332) the second expandable member 428 can be compressed or collapsed.

When in its expanded configuration as shown in FIG. 5, the second expandable member 428 has an elongated shape and defines an interior region 446 in fluid communication with the openings 429. The second expandable member 428 also defines a distal opening 448 that is in fluid communication with the interior region 446. Thus, the expandable member 428 is open at its distal end facing the expandable member 426. The second expandable member 428 can be used as a capture cap during a recanalization procedure as described above for previous embodiments. For example, during a recanalization procedure as described above for recanalization device 300, the expandable member 428 can be used to prevent dislodged or disrupted portions of the blockage from migrating beyond or proximally of the expandable member 428 within the blood vessel. Further, when the recanalization device 400 is moved proximally back into the delivery catheter, the second expandable member 428 can collapse an portions of the disrupted blockage disposed within the interior region 446 of the second expandable ember 428 can be captured therein.

Figure 6:
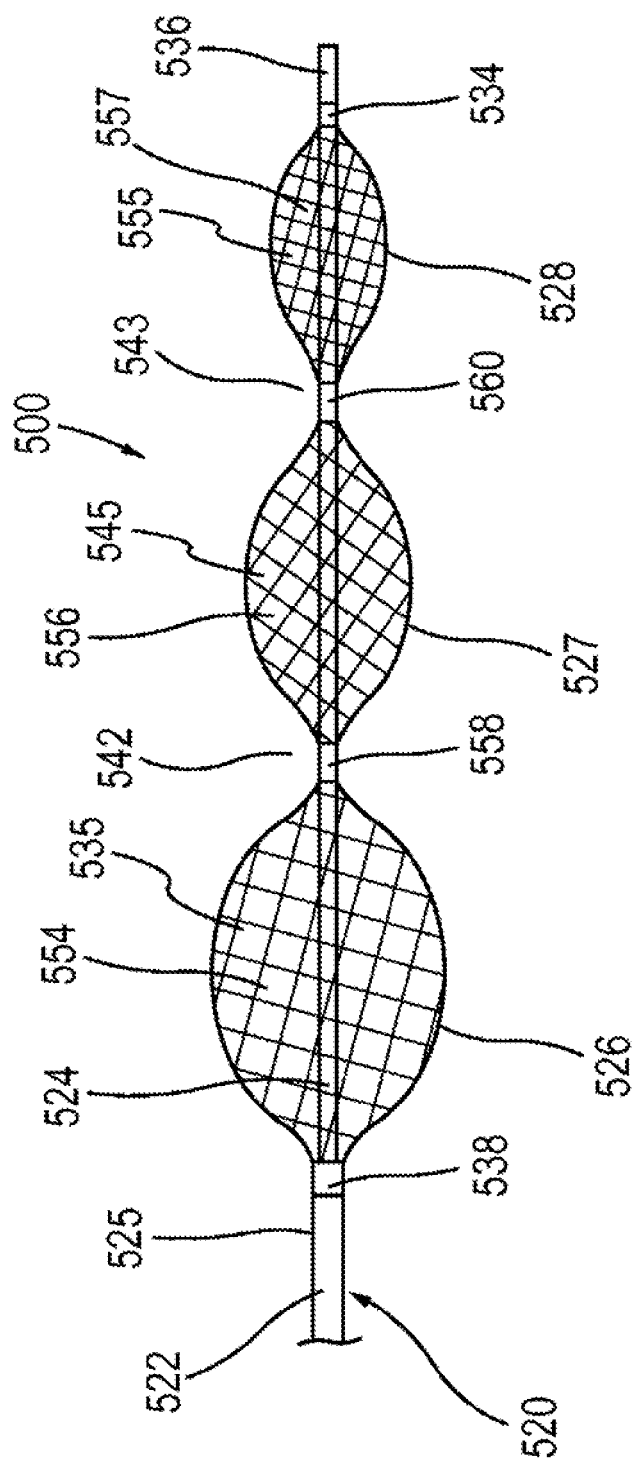
FIG. 6 is a side view of a portion of an expandable medical device, according to another embodiment, shown in an expanded configuration.

FIG. 6 illustrates a portion of another embodiment of a recanalization device. A recanalization device 500 (also referred to herein as "recanalization device" or "medical device") includes a first expandable member 526, a second expandable member 527 and a third expandable member 528 each coupled to an actuation member 520. The actuation member 520 includes a tubular member 522 that defines a lumen (not shown) between a proximal end and a distal end of the tubular member 522, and an elongate member 524 movably disposed within the lumen of the tubular member 522. As with previous embodiments, the actuation member 520 can optionally be coupled on a proximal end portion to a controller device (not shown), such as, for example, a hand-held controller as described above.

A proximal end portion of the first expandable member 526 is coupled to a distal end portion 525 of the tubular member 522 at attachment 538, and a distal end portion of the expandable member 526 and a proximal end portion of the second expandable member 527 are coupled to the elongate member 524 at attachment 558. A distal end portion of the second expandable member 527 and a proximal end portion of the third expandable member 528 are coupled to the elongate member 524 at attachment 560, and a distal end portion of the third expandable member 528 is coupled to a distal end portion 536 of the elongate member 524 at attachment 534.

The first expandable member 526, second expandable member 527 and third expandable member 528 can be coupled to the actuation member 520 with, for example, a clamp, clip, bonding, heat sealing, or other suitable coupling mechanism. The first expandable member 526, second expandable member 527 and third expandable member 528 can each be formed with a shape-memory material and have a collapsed configuration (not shown) and a biased expanded configuration as shown in FIG. 6. When in their collapsed configurations, the first expandable member 526, second expandable member 527 and third expandable member 528 each have a smaller outer perimeter or outer diameter than when in their expanded configuration. The first expandable member 526, second expandable member 527 and third expandable member 528 can each be formed with a mesh or braided material.

The first expandable member 526 defines multiple openings 535 and has a preformed expanded configuration that defines an interior region 554 in fluid communication with the multiple openings 535. The second expandable member 527 defines multiple openings 545 and has a preformed expanded configuration that defines an interior region 556 in fluid communication with the multiple openings 545. The third expandable member 527 defines multiple openings 555 and has a preformed expanded configuration that defines an interior region 557 in fluid communication with the multiple openings 555.

In this embodiment, each of the interior regions 554, 556 and 557 are separate from each other. In other words, the interior regions 554, 556 and 557 are not in fluid communication with each other. As shown in FIG. 6, a first annular capture region 542 is defined between the first expandable member 526 and the second expandable member 527, and a second annular capture region 543 is defined between the second expandable member 527 and the third expandable member 528.

The recanalization device 500 can be used to recanalize a vessel in a similar manner as described for previous embodiments. For example, the recanalization device 500 can be used to disrupt a blockage within a vessel and portions of the disrupted blockage can enter through the openings 535, 545 and 555 and be contained within the interior regions 554, 556 and 557. The recanalization device 500 can be rotated as previously described to further disrupt the blockage. As described above for previous embodiments, in some embodiments, the shape of the first expandable member 526, second expandable member 527 and third expandable member 528 can be further changed by pulling the elongate member 524 proximally and holding the tubular member 522 stationary, or moving the tubular member 522 distally and holding the elongate member stationary, or moving the elongate member 524 proximally while moving the tubular member 522 distally.

Figure 7:
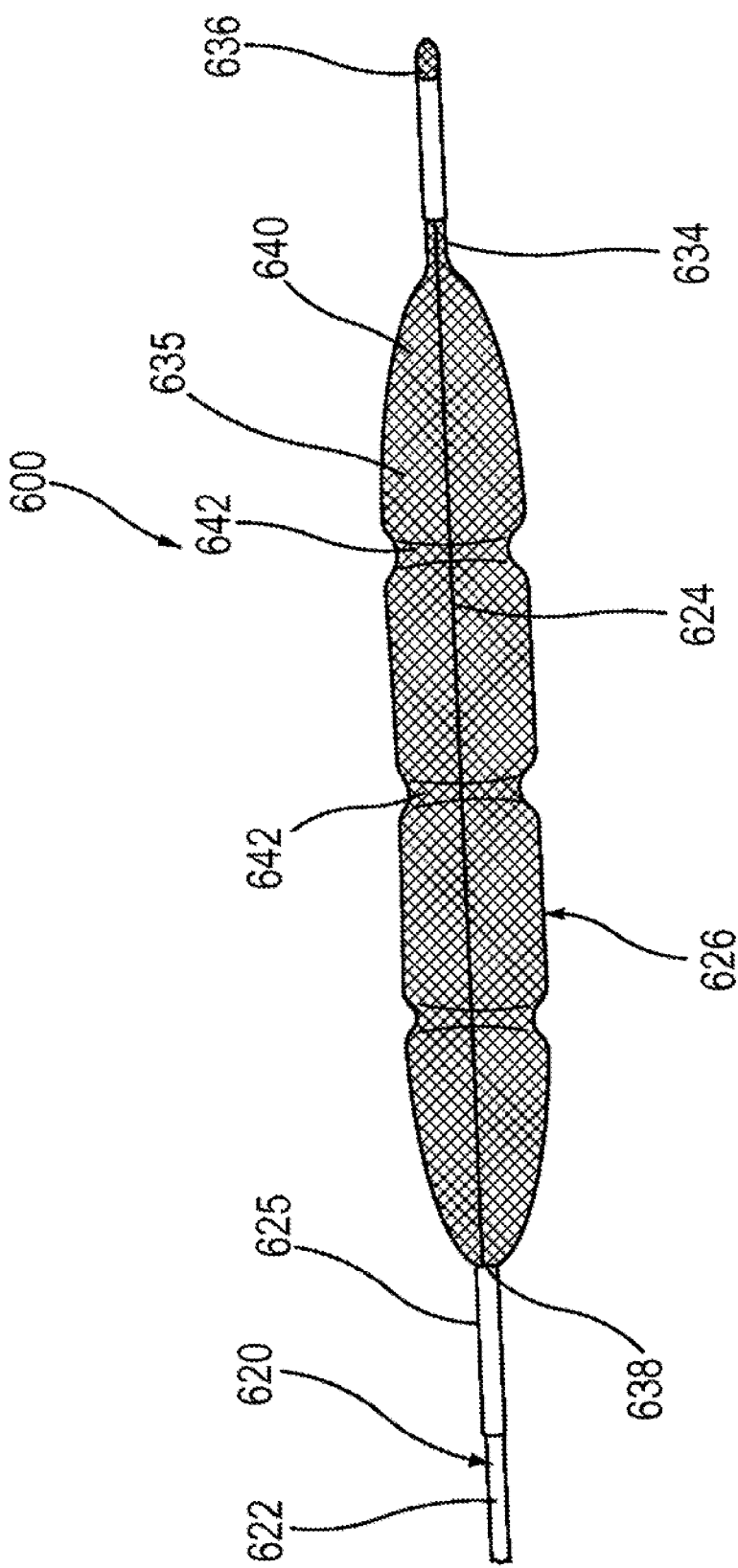
FIG. 7 is a side view of a portion of a medical device, according to another embodiment, shown in an expanded configuration.

FIG. 7 illustrates a portion of another embodiment of a recanalization device. A recanalization device 600 (also referred to herein as "recanalization device" or "medical device") includes an expandable member 626 coupled to an actuation member 620. The actuation member 620 includes a tubular member 622 that defines a lumen (not shown) between a proximal end and a distal end of the tubular member 622, and an elongate member 624 movably disposed within the lumen of the tubular member 622. The actuation member 620 can optionally be coupled on a proximal end portion to a controller device (not shown), such as, for example, a hand-held controller as described above.

A proximal end portion of the expandable member 626 is coupled to a distal end portion 625 of the tubular member 622 at attachment 638, and a distal end portion of the expandable member 626 is coupled to a distal end portion 636 of the elongate member 624 at attachment 634. The expandable member 626 can be attached with, for example, a clamp, clip, bonding, heat sealed, or other suitable coupling mechanism. As described above for the previous embodiment, the expandable member 626 can be formed with a mesh or braided material such that a wall of the expandable member 626 defines multiple openings or interstices 635. The expandable member 626 can have a collapsed or compressed configuration (not shown) and an expanded configuration as shown in FIG. 7. When in the collapsed configuration, the expandable member 626 has a smaller outer perimeter or outer diameter than when in the expanded configuration. When in the expanded configuration, the expandable member 626 defines an interior region 640 in fluid communication with the multiple openings 635.

The expandable member 626 can be formed with a shape-memory material such that it is biased into its expanded configuration when not restrained and can be inserted into a lumen of a delivery catheter to move to its compressed configuration. In this embodiment, the expandable member 626 defines capture regions 642 along an exterior surface that are preformed in the mesh material of the expandable member 626.

The shape of the expandable member 626 can be changed by pulling the elongate member 624 proximally and holding the tubular member 622 stationary, or moving the tubular member 622 distally and holding the elongate member 624 stationary, or moving the elongate member 624 proximally while moving the tubular member 622 distally. Such action can cause the expandable member 626 to at least partially collapse in a longitudinal direction capturing any portions of material within the capture regions 642. The recanalization device 600 can be used to clear a blockage in a recanalization procedure in the same or similar manner as described above for previous embodiments.

FIG. 8 illustrates an embodiment of a recanalization device including a proximal capture cap similar to the recanalization device 400 and FIG. 9 illustrates an embodiment of a recanalization device including a distal capture cap similar to the recanalization device 200'. A recanalization device 700 can include all the same features and functions as described above for recanalization device 400. For example, the recanalization device 700 includes a first expandable member 726 coupled at a proximal end portion to a tubular member 722 and is coupled at a distal end portion to a distal end portion of an elongate member 724 that is movably disposed within a lumen of the tubular member 722. The recanalization device 700 is shown in an expanded configuration and can be moved between a compressed or collapsed configuration and the expanded configuration in the same or similar manner as described above for previous embodiments. In this embodiment, the recanalization device 700 includes a second expandable member 728 coupled to the tubular member 722 proximal of the expandable member 726 at attachment 764.

The first expandable member 726 can be configured the same as or similar to and function the same as or similar to, for example, the expandable member 426. The second expandable member 728 can be formed with a mesh or braided material that defines multiple openings as described above for other embodiments. The second expandable member 728 can be formed with a shape-memory material such that it is biased into an expanded or open configuration as shown in FIG. 8, and can be moved to a compressed or closed configuration (not shown).

When in its expanded configuration as shown in FIG. 8, the first expandable member 726 defines a capture region 742 and a capture region 743 is defined between the first expandable member 726 and the second expandable member 728. The second expandable member 728 is substantially cup shaped or parabolic shaped and defines an interior region configured to receive portions of disrupted blockage material. The second expandable member 728 also defines a distal opening 748 that is in fluid communication with the interior region. The second expandable member 728 can be used as a capture cap during a recanalization procedure as described above for previous embodiments. For example, during a recanalization procedure as described above, the second expandable member 728 can be used to prevent dislodged or disrupted portions of the blockage from migrating beyond or proximally of the second expandable member 728.

A recanalization device 800 illustrated in FIG. 9 includes a first expandable member 826 coupled at a proximal end portion 838 to a tubular member 822 and is coupled at a distal end portion to an elongate member 824 that is movably disposed within a lumen of the tubular member 822. The recanalization device 800 is shown in an expanded configuration and can be moved between a compressed or collapsed configuration and the expanded configuration in the same or similar manner as described above for previous embodiments. In this embodiment, the recanalization device 800 includes a second expandable member 828 coupled to a distal end portion 836 of the elongate member 822 distal of the first expandable member 826.

The first expandable member 826 and the second expandable member 828 can each be formed with a mesh or braided material that defines multiple openings as described above for previous embodiments. The first expandable member 826 and the second expandable member 828 can each be formed with a shape-memory material such that they are biased into an expanded configuration as shown in FIG. 9, and can be moved to a compressed or closed configuration (not shown).

When in its expanded configuration as shown in FIG. 9, a capture region 842 is defined between the first expandable member 826 and the second expandable member 828 configured to receive portions of disrupted blockage material. The second expandable member 828 also defines an interior region configured to receive portions of disrupted blockage material. The second expandable member 828 also defines a proximal opening and can be used as a capture cap during a recanalization procedure as described above for previous embodiments. For example, during a recanalization procedure as described above, the second expandable member 828 can be used to prevent dislodged or disrupted portions of the blockage from migrating distally of the second expandable member 828.

Figure 10A:
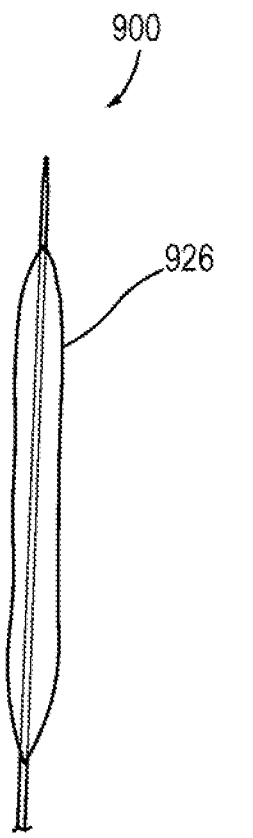
FIG. 10A is a side view of a portion of a medical device, according to another embodiment, shown in a collapsed configuration.
Figure 10B:
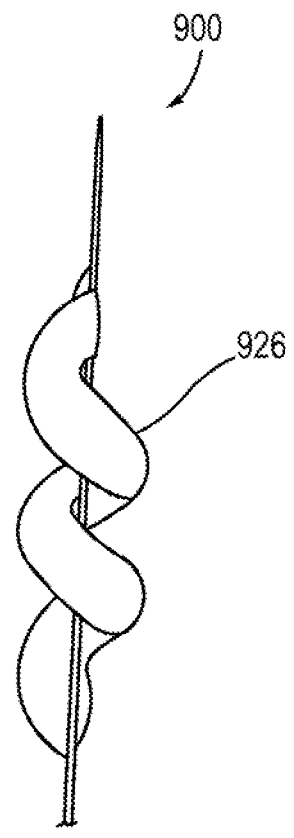
FIG. 10B is a side view of a portion of the medical device of FIG. 10A shown in an expanded and contoured configuration.

FIG. 10A illustrates a recanalization device 900 with an expandable member 926 shown in a collapsed configuration, and FIG. 10B illustrates the recanalization device 900 with the expandable member 926 shown in an expanded configuration and twisted to form a helical contoured shape. The recanalization device 900 can be configured the same as or similar to, and can be used in the same or similar manner, as described above for previous embodiments.

FIGS. 11A-11D illustrate an embodiment of a recanalization device with an expandable member formed with varying density. A recanalization device 1000 (also referred to herein as "recanalization device" or "medical device") includes an expandable member 1026 coupled to an actuation member 1020. The actuation member 1020 includes a tubular member 1022 that defines a lumen (not shown) between a proximal end and a distal end of the tubular member 1022, and an elongate member 1024 movably disposed within the lumen of the tubular member 1022. The actuation member 1020 can optionally be coupled on a proximal end portion to a controller device (not shown), such as, for example, a hand-held controller as described above. The recanalization device 1000 can be inserted through a lumen (not shown) of a catheter or sheath 1032 (see e.g., FIGS. 11B-11D), which will compress the expandable member 1026 into a collapsed or compressed configuration (not shown).

A proximal end portion of the expandable member 1026 is coupled to a distal end portion of the tubular member 1022 at attachment 1038, and a distal end portion of the expandable member 1026 is coupled to a distal end portion of the elongate member 1024 at attachment 1034.

As described above for previous embodiments, the expandable member 1026 can be formed with a mesh or braided material such that a wall of the expandable member 1026 defines multiple openings or interstices. In this embodiment, the expandable member 1026 is formed with a first mesh material that has a first density defining multiple openings 1035 and with a second mesh material having a second density defining multiple openings 1039. The expandable member 1026 includes sections 1066 along a length of the expandable member 1026 formed with the first mesh material, and sections 1068 along its length formed with the second mesh material.

Figure 11C:
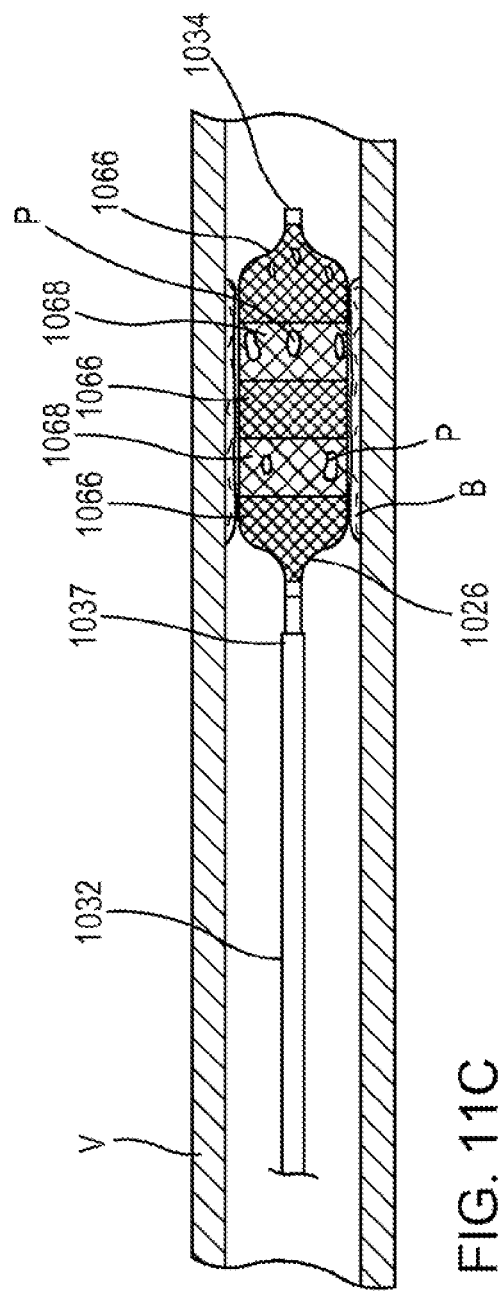
FIG. 11C is a side view of the medical device of FIG. 11A shown in an expanded configuration and disposed within a blood vessel.

The expandable member 1026 can have a collapsed or compressed configuration (not shown) and an expanded configuration (see e.g., FIG. 11C). When in the collapsed configuration, the expandable member 1026 has a smaller outer perimeter or outer diameter than when in the expanded configuration. When in the expanded configuration, the expandable member 1026 defines an interior region 1040 (see e.g., FIG. 11A) in fluid communication with the multiple openings 1035 and 1039. The expandable member 1026 can be formed with a shape-memory material such that it is biased into its expanded configuration when not restrained and can be inserted into the lumen of the delivery catheter 1032 to move to its compressed configuration.

In use, the catheter 1032 can be inserted through a blood vessel V and a distal end 1037 of the catheter 1032 can be positioned near a blockage B (see e.g., FIG. 11B). The expandable member 1026 can be moved out the distal end 1037 of the catheter 1032 by moving the actuation member 1020 (i.e., the tubular member 1022 and the elongate member 1024) distally through the blockage B and the expandable member 1026 can begin to assume its biased expanded configuration as shown in FIG. 11B. As the expandable member 1026 moves to its expanded configuration, the expandable member 1026 can contact and exert a force on the blockage B such that the blockage B is compressed and portions P of the blockage B are moved through the openings 1035 and 1039 of the expandable member 1026 and into the interior region 1040 of the expandable member 1026, as shown in FIG. 11C.

Figure 11D:
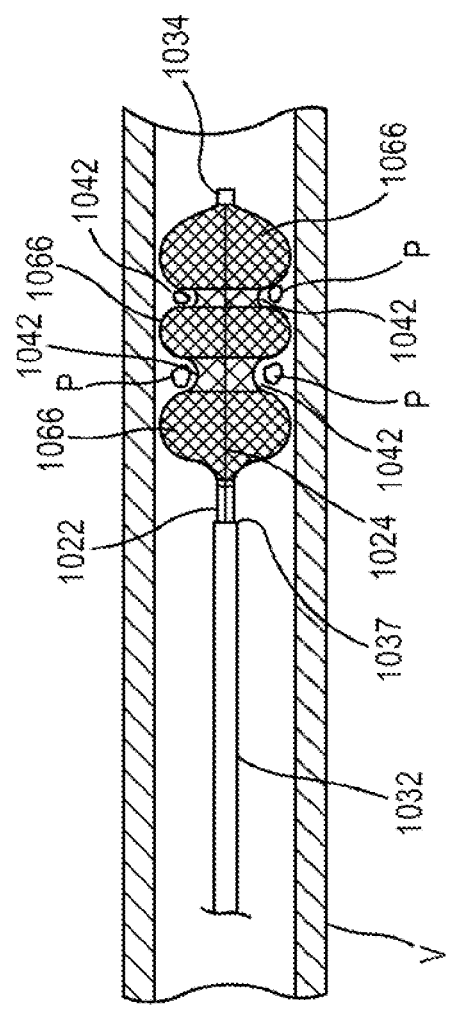
FIG. 11D is a side view of the medical device of FIG. 11A shown in an expanded and contoured configuration and disposed within a blood vessel.

As described above for previous embodiments, the expandable member 1026 can optionally be rotated to further disrupt the blockage B. In addition, the expandable member 1026 can be moved to a contoured or tortuous shape (as shown in FIG. 11D) by rotating the tubular member 1022 and/or elongate member 1022 relative to the other, or both can be rotated in opposite directions. As shown in FIG. 11D, the expandable member 1026 defines capture regions 1042 that can received dislodged or disrupted portions P of blockage B. When the disruption procedure is completed, the elongate member 1024 can be pulled proximally such that the expandable member 1026 partially collapses in a longitudinal direction (e.g., parallel with an axis defined by the blood vessel V) and the portions P are captured or trapped by the expandable member 1026. The expandable member 1026 can then be pulled proximally (e.g., by pulling the tubular member 1022 and the elongate member 1024) back into the lumen of the catheter 1032 with the portions P trapped within capture regions 1042 and the portions P captured within the interior region 1040 of the expandable member 1026.

Figure 12A:
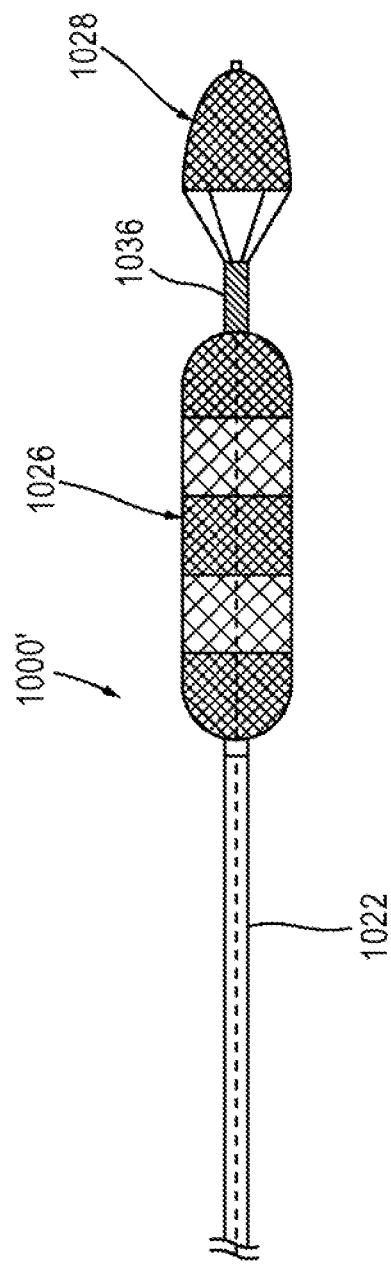
FIG. 12A is a side view of a medical device according to another embodiment, shown in an expanded configuration.
Figure 12B:
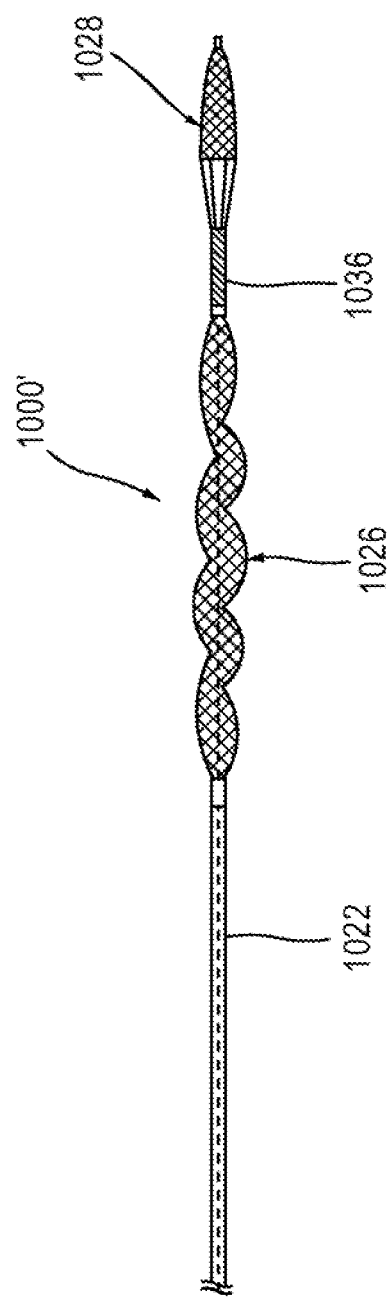
FIG. 12B is a side view of the medical device of FIG. 12A, shown in an expanded and contoured configuration.

FIGS. 12A and 12B illustrate a variation of the recanalization device 1000. The recanalization device 1000' includes the recanalization device 1000 with the addition of a second expandable member 1028 in the form of a distal capture cap coupled to a distal end portion 1036 of the elongate member 1024. The second expandable member 1028 can be configured the same as and function the same as or similar to the second expandable member 228 in FIG. 3. FIG. 12A shows the recanalization device 1000' in an expanded configuration and FIG. 12B shows the recanalization device 1000' expanded and twisted or rotated to a contoured configuration. The recanalization device 1000' can be moved to the expanded contoured configuration in a same or similar manner as described above for previous embodiments.

FIGS. 13A and 13B illustrate an embodiment of a recanalization device that includes an integral capture cap at a distal end portion of the recanalization device. A recanalization device 1100 includes an expandable member 1126 coupled to an actuation member 1120. The actuation member 1120 includes a tubular member 1122 and an elongate member 1124 movably disposed within a lumen 1123 of the tubular member 1122. As with previous embodiments, a proximal end portion of the expandable member 1126 is coupled to a distal end portion of the tubular member 1122 at attachment location 1138 and a distal end portion of the expandable member 1126 is coupled to a distal end portion 1136 of the elongate member 1124 at attachment location 1134.

The expandable member 1126 can be formed with the same materials and include the same features and functions as previous embodiments. In this embodiment, the expandable member 1126 includes a first portion 1150 that defines a first interior region 1154 and a second portion 1152 that defines a second interior region 1156. The second portion 1152 is in the form of an integral capture cap disposed at a distal end portion of the expandable member 1126. The capture cap 1128 can be formed or woven, for example, with the same filaments that form the expandable member 1126. A capture region 1142 is defined in the space between the expandable member 1126 and the capture cap 1128. The first portion 1150 defines multiple openings 1135 in a wall of the first portion 1150 that are in fluid communication with the first interior region 1154 and the second portion 1152 defines multiple openings 1139 that are in fluid communication with the second interior region 1156.

The expandable member 1126 can be moved between a collapsed configuration for insertion into a vessel and/or a lumen of a catheter or sheath, and an expanded configuration for use during a recanalization procedure as described herein. FIG. 13A illustrates the expandable member 1126 in an expanded configuration and FIG. 13B illustrates the expandable member 1126 shown partially collapsed within a lumen 1133 of a delivery catheter 1132. As shown in FIG. 13B, portions P of bodily tissue from a blockage can be captured within the capture region 1142, the first interior region 1154 and the second interior region 1156 and as the expandable member 1126 is drawn back into the lumen 1133 of the catheter 1132, the portions P are trapped pulled therein with the expandable member 1126.

Figure 14A:
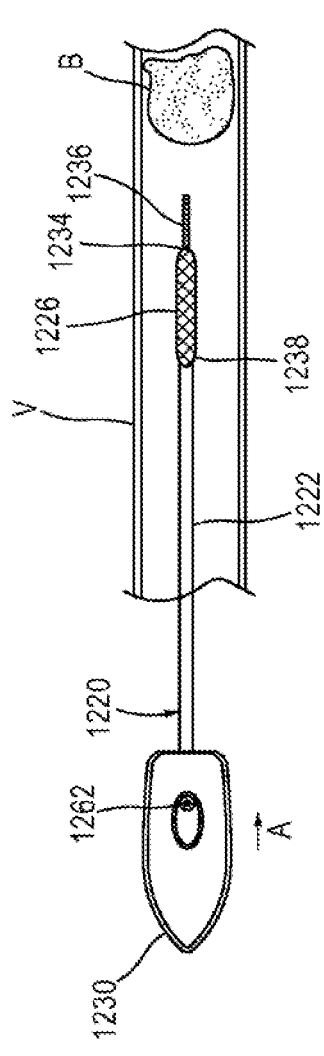
FIG. 14A is a side view of a medical device according to another embodiment, shown in a collapsed configuration and being inserted into a blood vessel.
Figure 14B:
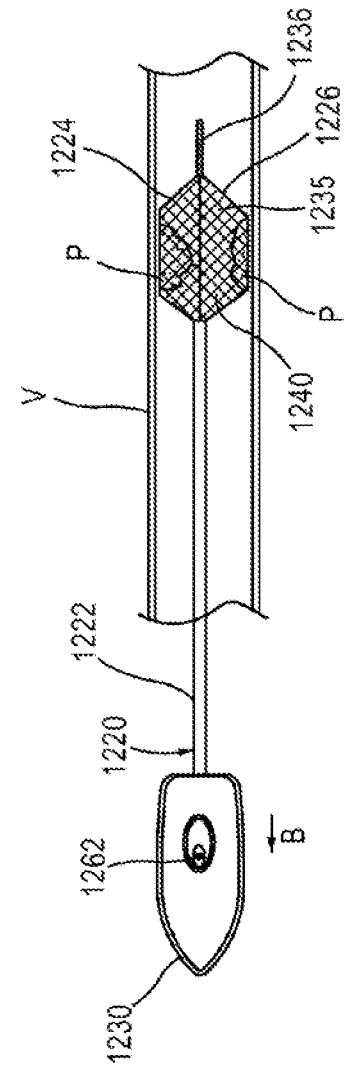
FIG. 14B is a side view of the medical device of FIG. 14A, shown in an expanded configuration disposed within a blood vessel adjacent a blockage.
Figure 14C:
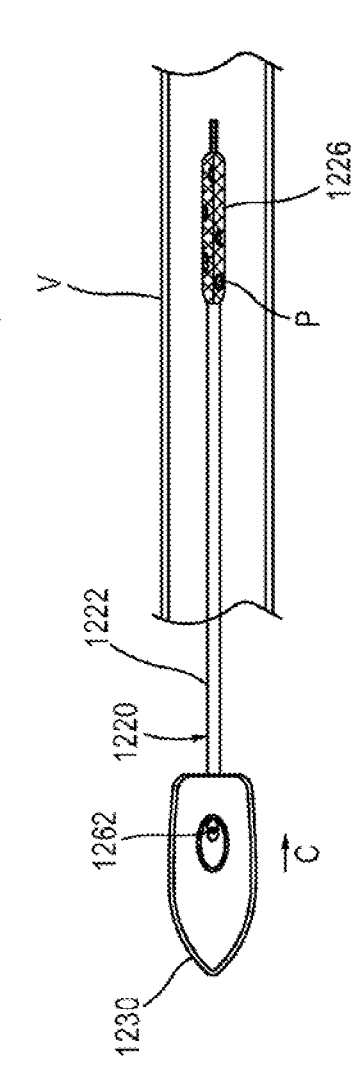
FIG. 14C is a side view of the medical device of FIG. 14A, shown in a collapsed configuration disposed within a blood vessel.

FIGS. 14A-14C illustrate an embodiment of a recanalization device being deployed within a blood vessel without the use of a delivery catheter. A recanalization device 1200 includes an expandable member 1226 coupled to an actuation member 1220. The actuation member 1220 includes a tubular member 1222 and an elongate member 1224 movably disposed within a lumen (not shown) of the tubular member 1222. A proximal end portion of the expandable member 1226 is coupled to a distal end portion of the tubular member 1222 at attachment location 1238 and a distal end portion of the expandable member 1226 is coupled to a distal end portion 1236 of the elongate member 1224 at attachment location 1234. The actuation member 1120 is coupled to a controller device 1230 that can be used to control movement of the elongate member 1224 relative to the tubular member 1222 as described in more detail below.

The expandable member 1226 can be formed with the same materials and include the same features and functions as previous embodiments. In this embodiment, the expandable member 1226 defines multiple openings 1235 in fluid communication with an interior region 1240 (see e.g., FIG. 14B). The openings 1235 can be configured and sized to encourage material from a blockage (e.g., a blood clot) to enter the expandable member 1226 for removal from a vessel.

The expandable member 1226 can be moved between a collapsed configuration for insertion into a vessel as shown in FIG. 14A, and an expanded configuration for use during a recanalization procedure as shown in FIG. 14B. In this embodiment, to move the expandable member 1226 to the collapsed configuration, the operator or user of the recanalization device 1200 can move an actuation button 1262 on the controller 1230 distally or in a direction A (see FIG. 14A) toward a vessel V in which the recanalization device 1200 is being disposed. The button 1262 is operatively coupled to the elongate member 1224 such that when the button 1262 is moved distally, the elongate member 1224 will move distally relative to the tubular member 1222. Because the expandable member 1226 is coupled at its proximal end to the tubular member 1222, this action will cause the expandable member 1226 to elongate or collapse as shown in FIG. 14A. The user can maneuver the distal end portion 1236 to a desired location at or near a blockage B within the vessel V.

The expandable member 1226 can then be moved to its expanded configuration while disposed at the desired treatment site by moving button 1262 proximally in a direction B as shown in FIG. 14B. As described above for previous embodiments, as the expandable member 1226 expands, it can contact and exert a force on the blockage B such that portions P of the blockage B are disrupted and pass through the openings 1240 of the expandable member 1226 as shown in FIG. 14B. When the recanalization procedure is complete, the expandable member 1226 can be moved to a collapsed configuration by moving the button 1262 distally in a direction C as shown in FIG. 14C. As the expandable member 1226 is moved to the collapsed configuration, the portions P of the blockage B disposed within the interior region 1240 will be captured by the expandable member 1226. The expandable member 1226 can then be withdrawn from the vessel V.

FIGS. 15A-15C illustrate an embodiment of a recanalization device that can be used to perfuse an oxygenated or superoxygenated blood distal to a blockage within a vasculature to reduce or eliminate ischemia during the procedure by providing the region cut off by blood supply fresh oxygenated blood to keep the tissue alive. A recanalization device 1300 includes an expandable member 1326 coupled to an elongate member 1324. The expandable member 1326 can be configured the same as expandable members described above for previous embodiments. For example, the expandable member 1326 can be formed with a shape memory material such that it has a biased expanded configuration (e.g., as shown in FIG. 15A) and can be moved to a compressed or collapsed configuration by restraining the expandable member 1326 within a lumen of a delivery catheter. In this embodiment, the expandable member 1326 defines a lumen extending between a proximal end and a distal end of the elongate member 1324 and that is in fluid communication with an opening 1364 on the distal end of the expandable member 1326 and an opening 1366 on the proximal end of the expandable member 1326. The proximal end of the expandable member 1326 can be coupled to a source of oxygenated or superoxygenated blood (not shown).

In use, the recanalization device 1300 can be inserted through a lumen 1333 of a delivery catheter 1332 and inserted into a vessel V as shown in FIGS. 15B and 15C. The expandable member 1326 can be moved out a distal end 1337 of the delivery catheter 1332 and positioned within a blockage B to be treated. As the expandable member 1326 is moved out of the delivery catheter 1332 it can assume its biased expanded configuration as described above for previous embodiments. As the expandable member 1326 expands it can contact and compress the blockage B and portions of the blockage can enter into an interior region of the expandable member through openings 1335 defined in the mesh material of the expandable member 1326. While the blockage is being cleared, oxygenated blood can be perfused through the lumen of the elongate member 1326 and out the distal opening 1364.

Figure 16:
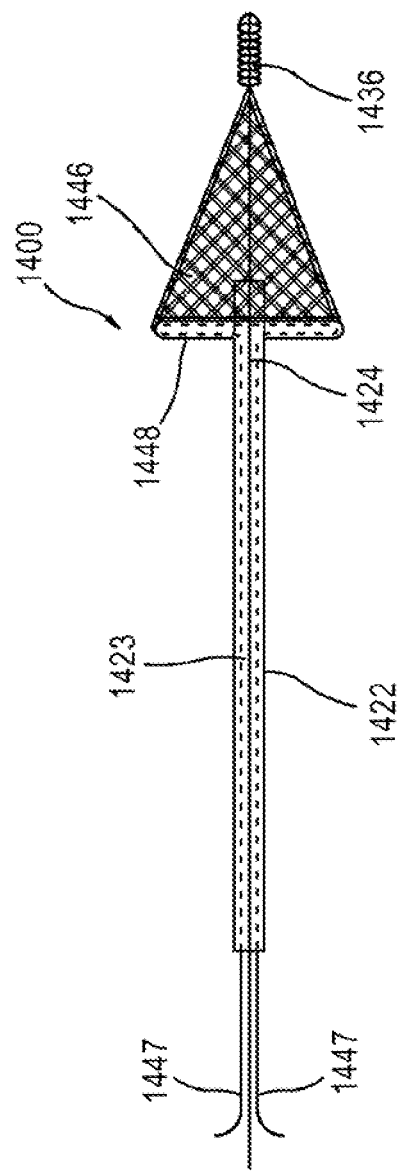
FIG. 16 is a side view of a medical device according to another embodiment, shown in an expanded configuration.
Figure 17:
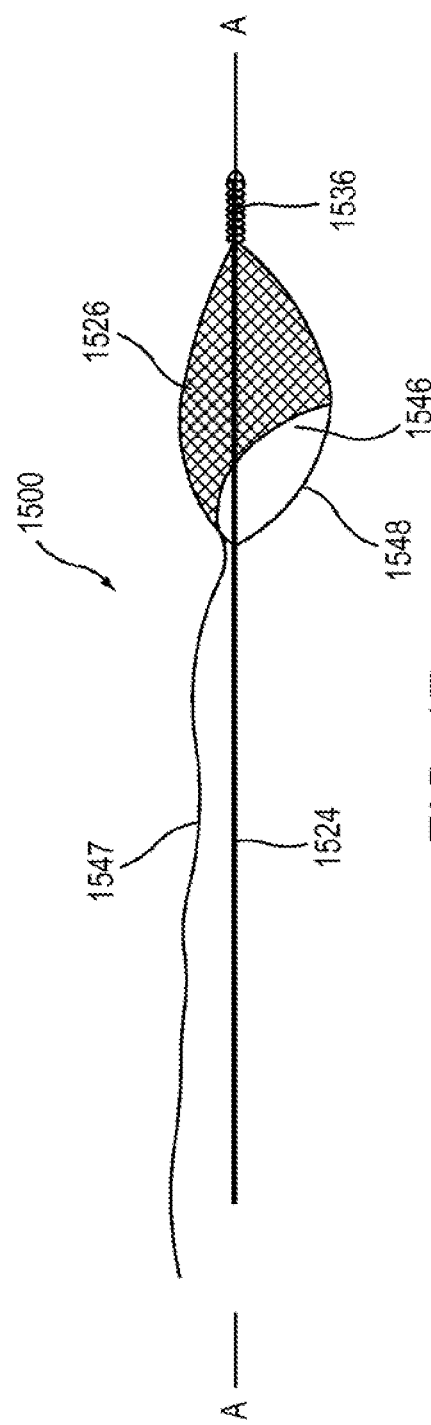
FIG. 17 is a side view of a medical device according to another embodiment, shown in an expanded configuration.
Figure 18:
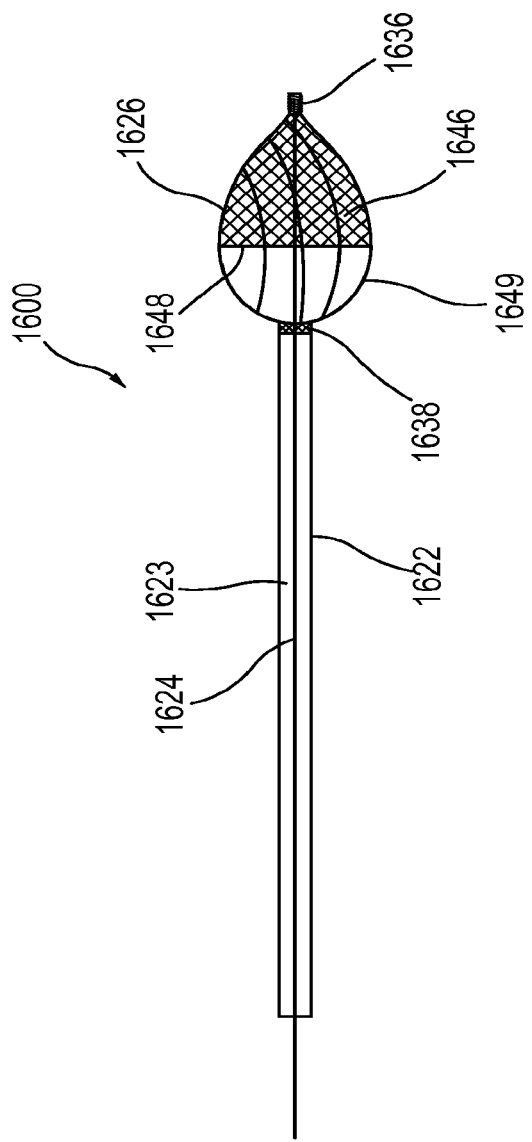
FIG. 18 is a side view of a medical device according to another embodiment, shown in an expanded configuration.

FIGS. 16-18 each illustrate a different embodiment of a recanalization device that includes a distal capture cap. A recanalization device 1400 shown in FIG. 16 includes an expandable member 1428 coupled at a proximal end portion to a distal end portion of a tubular member 1422 and coupled at a distal end portion to a distal end portion 1436 of an elongate member 1424. The elongate member 1424 is movably disposed within a lumen 1423 of the tubular member 1422. In this embodiment, the expandable member 1426 is formed with two layers of braid or mesh material and defines an opening 1448 on a proximal end in fluid communication with an interior region 1446. A looped control wire 1447 is coupled to the expandable member 1426 adjacent the opening 1448 and extends through the lumen 1423 of the tubular member 1422 and can be used to move the expandable member 1426 to a collapsed configuration as described below.

As described above for previous embodiments, the expandable member 1426 can be moved from a collapsed configuration for insertion into a vessel, and an expanded configuration (as shown in FIG. 16) in which portions of a blockage within the vessel can be captured within the interior region 1446. To move the expandable member 1426 to the collapsed configuration, the looped control wire 1447 can be pulled proximally to cinch or close the expandable member 1426. Thus, during a recanalization procedure as described herein, portions of a blockage can enter through the opening 1448 and be disposed with the interior region 1446 while the expandable member 1426 is in the expanded configuration. The expandable member 1426 can then be moved to the collapsed configuration capturing the portions of the blockage for removal from the vessel.

FIG. 17 illustrates a recanalization device 1500 shown in an expanded configuration. The recanalization device 1500 includes an expandable member 1526 coupled at a distal end portion to a distal end portion 1536 of an elongate member 1524. The elongate member 1524 can be movably disposed within a lumen of a tubular member (not shown) as described for previous embodiments. In this embodiment, the expandable member 1526 is formed with a braid or mesh material and defines an opening 1548 on a proximal end portion in fluid communication with an interior region 1546. The opening 1548 is defined on a bias of the braid or mesh material such that the opening 1548 is disposed at an angle transverse to a longitudinal axis A of the elongate member 1524. A control wire 1547 is coupled to the expandable member 1526 adjacent the opening 1548 and can extend proximally outside of the patient's body and can be used to move the expandable member 1526 to a collapsed configuration. Control of closure of the opening 1548 can be facilitated by pulling the control wire 1547 proximally. Effecting closure on the bias or diagonal can provide a less bulky unit, which can make delivery and withdrawal of the recanalization device 1500 easier.

As described above for previous embodiments, the expandable member 1526 can be moved from a collapsed configuration for insertion into a vessel, and an expanded configuration (as shown in FIG. 17) in which portions of a blockage within the vessel can be captured within the interior region 1546. The expandable member 1526 can be moved to the collapsed configuration using the control wire 1547 a described above, capturing the portions of the blockage within the interior region 1546 for removal from the vessel.

FIG. 18 illustrates a recanalization device 1600 that includes an expandable member 1626 coupled at a distal end portion to a distal end portion 1636 of an elongate member 1624 and coupled at a proximal end portion to a distal end portion of a tubular member 1622 at attachment 1638. The elongate member 1624 is movably disposed within a lumen 1623 of the tubular member 1622. In this embodiment, the expandable member 1626 is formed with a braid or mesh material and defines an opening 1648 in fluid communication with an interior region 1646 and includes filaments or strands 1649 that extend from a perimeter of the opening 1648 to the proximal attachment 1638. The strands 1649 can be formed with a larger diameter than the filaments used to form the mesh or braid of the expandable member 1626 and can have a helical configuration. The larger diameter of the strands 1649 can assist in the closure of the expandable member 1626.

As described above for previous embodiments, the expandable member 1626 can be moved from a collapsed configuration for insertion into a vessel, and an expanded configuration (as shown in FIG. 18) in which portions of a blockage within the vessel can be captured within the interior region 1646. To move the expandable member 1626 to the collapsed configuration, the elongate member 1624 can be moved distally relative to the tubular member 1622 and/or the tubular member 1622 can be moved proximally relative to the elongate member 1622 as described above for previous embodiments.

A method of using a recanalization device as described herein in a procedure to clear a blockage within a vessel, can include advancing an expandable member of a recanalization device while in a collapsed configuration to a desired treatment site (e.g., a location of a blood clot or other blockage) within a blood vessel. The expandable member of the recanalization device is coupled to a core wire movably disposed within a hypotube as described herein. The expandable member can be positioned such that most, if not all of the openings and/or capture regions of the expandable member are disposed within the blockage region. The core wire is then retracted (moved proximally) within the hypotube to expand the expandable member, and at the same time form capture regions along an exterior of the expandable member. As the expandable member is expanded, the blockage (e.g., blood clot) is compressed by the expandable member against the walls of the vessel, which can restore blood flow to the vessel. The blockage material can be trapped within the capture regions and within an interior of the expandable member. The core wire can be pulled further proximally to achieve a desired structural rigidity for the expandable member and the portions of the blockage can be trapped between by the expandable member within the capture regions. The recanalization device and blockage material are retrieved together back into, for example, guide catheter for removal from the vessel.

Figure 19:
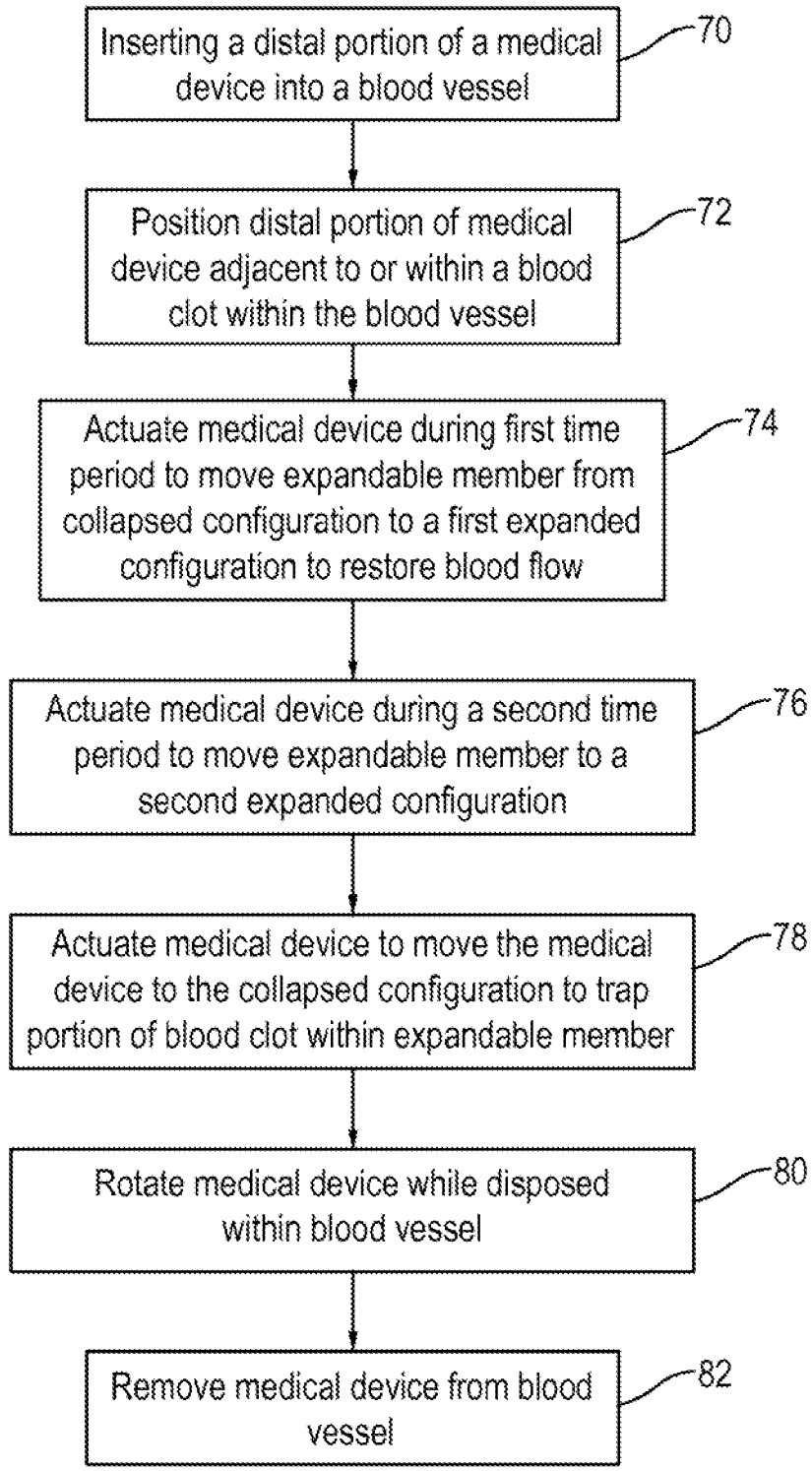
FIG. 19 is a flowchart illustrating a method of using a medical device for a recanalization procedure.

FIG. 19 is a flowchart illustrating another method of using a recanalization device as described herein to perform a recanalization procedure. The method includes at 70, inserting a distal portion of a medical device into a blood vessel. The medical device can include an elongate member and an expandable member coupled to a distal portion of the elongate member. The expandable member defines multiple openings in a wall of the expandable member and is in a collapsed configuration during the inserting. At 72, the distal portion of the medical device is positioned adjacent to or within a blood clot within the blood vessel. At 74, the medical device is actuated at a first time period to move the expandable member from the collapsed configuration to a first expanded configuration in which the expandable member defines an interior region in fluid communication with the multiple openings and such that the expandable member contacts the blood clot and at least a first portion of the blood clot enters through at least one of the openings and into the interior region of the expandable member. This action can restore blood flow through the blood vessel. At 76, the medical device is actuated at a second time period to move the expandable member from the first expanded configuration to a second expanded configuration in which the expandable member defines at least one capture region configured to receive a second portion of the blood clot therein. For example, the medical device can include a tubular member defining a lumen and the elongate member can be movably disposed within the lumen of the tubular member. The actuating the medical device at the second time period can include rotating at least one of the elongate member or the tubular member such that the expandable member is twisted into a tortuous configuration.

At 78, after the second time period, the medical device can be actuated again to move the expandable member to its collapsed configuration while disposed within the blood vessel such that at least a portion of the blood clot is trapped within the expandable member. At 80, the medical device can optionally be rotated while disposed within the blood vessel and in either the first expanded configuration or the second expanded configuration such that at least a third portion of the blood clot is moved through at least one of the multiple openings and into the interior volume of the expandable member.

In some embodiments, the expandable member is a first expandable member and the medical device can include a second expandable member coupled to the distal portion of the elongate member at a non-zero distance from the first expandable member. The first expandable member and the second expandable member can define a capture region between the first expandable member and the second expandable member. In such an embodiment, the medical device can be actuated such that the second expandable member is moved toward the first expandable member and at least one of the second portion of the blood clot or a third portion of the blood clot is trapped between the first expandable member and the second expandable member. In some embodiments, the elongate member can define a lumen and the method can include infusing one of oxygenated blood and superoxygenated blood through the lumen of the elongate member and into the blood vessel distal to the blood clot. At 82, the medical device can be removed from the blood vessel with captured portions of the blood clot contained within the expandable member.

In some embodiments, the devices described herein can be included in a kit. For example, a kit can include one or more recanalization devices, one or more delivery catheters or sheaths, various other devices that can assist in the stabilization or removal of an obstruction, instructions and/or a container for the contents of the kit.

The length of the expandable member (e.g., braid or mesh) can be variable depending on the assessed size of the obstruction and the amount of material to be retrieved in the case that the device is acting as a clot retriever. In addition to being affixed at the proximal and distal ends, the expandable member can be constricted at one or more points along a length of the expandable member. For example, the expandable member can be coupled along the hypotube at more than one location and/or coupled to the elongate member (e.g., core wire) at one more locations. If the expandable member is made of metal wire (e.g. NiTi wire), the expandable member may be heat treated after the expandable member is constricted at the hypotube (generally with a band or with wrapped wire, e.g. Platinum wire) at the one or more points. The constriction can be done to fix the bulges of the expandable member (e.g., the braid or mesh material) to a certain shape. The heat treatment may be desired where the sections of the expandable member (separated by the constriction points) are different lengths or diameters. Heat treatment of the expandable member braided wire may not be necessary, for example, where the tube is constricted at regular intervals along a length of the expandable member. The core wire can be made, for example, with any metal typically used for medical guidewires, including stainless steel or NiTi. The hypotube can be made, for example, with any metal or cable-formed hypotube, such as typically used in the medical arts for constructing tubes that carry pusher or core wires.

Constriction of the expandable member at intervals along the length of the expandable member can be done to establish compartments between regions of the expandable member. When delivered to a blood vessel, the core wire can extend out from the hypotube at the distal end and can be pushed out further distally so that the expandable member is compressed as much as possible for delivery. The constriction points can move along the core wire within the hypotube. The expandable member can be passed through the blockage, transverse to the blocking material. After the expandable member is positioned beyond the obstruction, the core wire can be pulled back (proximally), which begins the formation of compartments between the regions of the expandable member. The expandable member regions can expand outward to contact the vessel walls and to pull the obstructing material within compartments formed between the expandable member openings/spaces. Provisionally, the amount of obstructing material can serve as a guide to determine how many constriction points may be desired along the expandable member. For example, in some embodiments, the device can include, from 1 to about 10 constriction points.

The various devices described herein can be made of any material suitable for the defined purpose, including, for example, drawn filed tube DFT®. DFT is available as wire, cable or ribbon. Drawn filed tube DFT is a metal-to-metal composite developed to combine the desired physical and mechanical attributes of two or more materials into a single wire or ribbon system, which can be used for the core wire within the hypotube, or for the expandable member.

Filaments or wires for the device (either in the elongate member or the expandable member) can include, for example, gold, silver, platinum, titanium, titanium alloys, nitinol, platinum alloys, and tungsten. Outer materials for the hypotube (e.g., tubular member) or DFT wire can include, for example, MP35N, stainless steel, nitinol, cobalt chromium, titanium alloys, zirconium alloys, platinum, tantalum, and tungsten. For the braid or mesh (e.g., the expandable members), filaments can also include, for example, filaments of materials such as MP35N, stainless steel, nitinol, cobalt chromium, titanium alloys, zirconium alloys, platinum, tantalum, tungsten, polyester, polyethylene (PET), Dacron, PEEK, vectron, and suture materials. Each strand may have a diameter between 0.0005"-0.010", e.g., about 0.002". In some embodiments, an outer material of the mesh or braid can be formed with nitinol that is super elastic at body temperature, and an inner material can be radiopaque, or alternatively platinum wires may be included in the braid to provide additional radiopacity.

In some embodiments, the expandable members described herein can be formed with tubular braid, or sheets of woven filaments (forming a mesh, weave or fabric). The filaments can be wire or polymer or other suitable material. The expandable members can be braided wire (e.g. NiTi wire), and can include a mixture of wire types and wire sizes (e.g. NiTi and Platinum wire, and e.g. 0.001" wire braided with 0.00125" wire). The expandable members can also be made with polymer fibers, or polymer fibers and metal wire mixed together.

The mesh of the expandable members can be made by a variety of different forms, including but not limited to, braiding, weaving, welding, or laser cutting. The mesh can have an operating length, for example, in a range of about 0.5 mm to about 70 mm. In some embodiments, the mesh can have a length of 30 mm. In some embodiments, the mesh can have a diameter in a range of about 0.5-60 mm. In some embodiments, the mesh can have a diameter of about 5 mm when expanded. The mesh can have a single density or can have two or more densities. For example, in some embodiments, the number of variable densities can be in a range of about 2 to about 10. For example, a first density can be about 100 PPP and a second density can be about 40 PPI. (PPI=pics per inch). The braid pattern can be any pattern suitable, for example, a one-over-one configuration, or two-over-one configuration, etc. Strand count for the mesh can be in a range of about 4 strands to about 288 strands. In some embodiments, the strand count is about 48 strands. Common multiples of 4, 8, 16, 24, 32, 64, 72, 96, 128, 144, 192 and 288 strands for braid are available using commercial braiders.

A single expandable member can include wires of the same size or a combination of 2 different wire sizes. For example, the expandable member can have 24 wires of 0.001" and 24 wires of 0.0005". The thicker wires can impart additional strength to the expandable member and the thinner wire can provide density. In addition any combination of wire count, wire diameter, braid angle or pick per inch can be used to make the mesh of the expandable member.

A non limiting example of suitable delivery catheters that can be used include, for example, the Excelsior line of BSCI, the DAC catheter line of Concentric Medical and Rapidtransit of J&J. Use of oxygenated and superoxygenated blood is described in an article entitled Buying Time for Recanalization in Acute Stroke: Arterial Blood Infusion Beyond the Occluding Clot as a Neuroprotective Strategy Ribo et al, Barcelona, Spain (BA, MM), Jan. 28, 2008. Ribo et al describe a novel neuroprotective intra-arterial (IA) strategy that allows intermittent oxygenated blood perfusion beyond the occluding clot. In the case studied an almost total recovery was observed despite late complete recanalization (12 hours after onset), which suggests a neuroprotective effect of the technique.

CONCLUSION

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. The specific configurations of the various components can also be varied. For example, the size and specific shape of the various components can be different than the embodiments shown, while still providing the functions as described herein.

What is claimed is:

1. A method of treating an embolism comprising:
    delivering an embolectomy device to an embolism that at least, partially restricts blood flow through a blood vessel, wherein the embolectomy device comprises an expandable member having a first expandable portion, a second expandable portion, and a third expandable portion, each of the first expandable portion, the second expandable portion, and the third expandable portion comprising a mesh, the meshes of the first expandable portion and the third expandable portion having a first mesh density, the mesh of the second expandable portion having a second mesh density, the second mesh density being less than the first mesh density when the first expandable portion, the second expandable portion, and the third expandable portion are expanded to the same extent, wherein at least a portion of the expandable member is configured to expand outwardly to engage at least a portion of the embolism or blood vessel wall;
    deploying the embolectomy device within the embolism so as to restore blood flow through the embolism and, form a flow channel through the embolism while the expandable member of the embolectomy device is expanded, wherein the embolectomy device in a deployed configuration comprises first and third portions expanded to a greater extent than the second portion, the second expandable portion being disposed between the first and third expandable portions, and wherein the first and third expandable portions project radially outward beyond the second portion;
    moving the embolectomy device and at east a portion of the embolism along the blood vessel; and
    withdrawing the embolectomy device and at least a portion of the embolism from the blood vessel.

2. The method of claim 1, further comprising accessing the blood vessel of a patient, wherein delivering comprises inserting a delivery catheter containing the embolectomy device into the blood vessel to a clot of the embolism and positioning the delivery catheter through the clot.

3. The method of claim 2, further comprising deploying the embolectomy device from the delivery catheter, wherein at least a portion of the expandable member is positioned and expanded beyond the clot of the embolism.

4. The method of claim 3, wherein the expandable member is self-expanding when unconstrained from the delivery catheter within the blood vessel.

5. The method of claim 1, further comprising cutting into a material of the embolism with the embolectomy device.

6. The method of claim 1, wherein the expandable member defines at least one capture region on an external surface of the expandable member in the deployed configuration, the at least one capture region defined in part by the first and third portions which are expanded to a greater extent than the second portion in the deployed configuration.

7. The method of claim 6, further comprising disrupting and receiving at least a portion of the embolism with the at least one capture region.

8. The method of claim 6, wherein the expandable member defines a plurality of annular capture regions configured to disrupt and receive at least a portion of the embolus.

9. The method of claim 1, wherein the first expandable portion has a first outer perimeter, the second expandable portion has a second perimeter, and the third expandable portion has a third outer perimeter, wherein in the deployed configuration the second outer perimeter is smaller than the first and third outer perimeters such that the expandable member defines at least one capture region between the first and third outer perimeters.

10. The method of claim 9, further comprising disrupting and receiving at least a portion of the embolism with the at least one capture region.

11. The method of claim 1, wherein deploying the expandable member generates an outwardly expanding radial force such that the expandable member can expand through a material of the embolism and displace or masticate the material in the blood vessel.

12. The method of claim 1, wherein deploying the embolectomy device within the embolism comprises expanding the embolectomy device so that the expandable member is biased to a predetermined shape.

13. The method of claim 1, wherein the expandable member comprises woven or braided filaments or strands of metal or polymer that form a mesh configuration.

14. The method of claim 13, wherein the embolectomy device comprises a continuous mesh and the first expandable portion, the second expandable portion, and the third expandable portion are integrally formed of the mesh, wherein in the deployed configuration the mesh is expanded to a greater extent at the first and third portions than at the second portion.

15. A method of treating an embolism comprising:
    accessing a vessel of a patient;
    delivering a clot treatment device to a clot of an embolism that at least partially restricts blood flow through a blood vessel with a delivery catheter, wherein the clot treatment device comprises an expandable member having a first portion with a first outer perimeter, a second portion with a second outer perimeter, and a third portion with a third outer perimeter, each of the first portion, the second portion, and the third portion comprising a mesh, the meshes of the first portion and the third portion having a first mesh density, the mesh of the second portion having a second mesh density, the second mesh density being less than the first mesh density when the first portion, the second portion, and the third portion are expanded to the same extent, wherein the second portion is disposed between the first and third portions, and wherein at least a portion of the expandable member is configured to expand outwardly to engage at least a portion of the embolism or blood vessel wall;

positioning the clot treatment device within the embolism;

radially expanding the expandable member against the clot so as to restore blood flow through the clot in the blood vessel while the expandable member of the clot treatment device is expanded, wherein the clot treatment device in a deployed configuration comprises first and third portions expanded to a greater extent than the second portion, and wherein the second outer perimeter is smaller than the first and third outer perimeters such that the expandable member defines at least one capture region between the first and third outer perimeters;

disrupting at least a portion of the clot with the at least one capture region of expandable member;

retrieving at least a portion of the clot with the at least one capture region of the expandable member; and withdrawing the clot treatment device and at least a portion of the clot from the blood vessel.

16. The method of claim 15, wherein the expandable member is self-expanding when unconstrained from the delivery catheter within the blood vessel.

17. The method of claim 15, wherein the expandable member defines a plurality of annular capture regions on an external surface of the expandable member in the deployed configuration to disrupt and retrieve at least the portion of the clot.

\* \* \* \* \*